US009631024B2

(12) United States Patent
Reyes et al.

(10) Patent No.: US 9,631,024 B2
(45) Date of Patent: Apr. 25, 2017

(54) ANTIBODIES THAT BIND LGR4, THEIR USE IN INHIBITING NEOPLASTIC CELLS AND IN TREATING TUMORS

(71) Applicant: Bionomics Inc., San Diego, CA (US)

(72) Inventors: Christopher L. Reyes, San Diego, CA (US); Kristen M. Smith, San Clemente, CA (US); Peter Chu, San Diego, CA (US); Lioudmila A. Campbell, San Diego, CA (US); Eric Ailor, San Diego, CA (US)

(73) Assignee: Bionomics, Inc., San Diego, CA (US)

( * ) Notice: Subject to any disclaimer, the term of this patent is extended or adjusted under 35 U.S.C. 154(b) by 0 days.

(21) Appl. No.: 14/741,696

(22) Filed: Jun. 17, 2015

(65) Prior Publication Data
US 2016/0046723 A1    Feb. 18, 2016

Related U.S. Application Data

(60) Provisional application No. 62/015,980, filed on Jun. 23, 2014.

(51) Int. Cl.
*C07K 16/30* (2006.01)
*C07K 16/28* (2006.01)
*A61K 39/395* (2006.01)
*A61K 39/00* (2006.01)

(52) U.S. Cl.
CPC ........ *C07K 16/30* (2013.01); *A61K 39/39558* (2013.01); *C07K 16/2896* (2013.01); *A61K 2039/505* (2013.01); *C07K 2317/24* (2013.01); *C07K 2317/565* (2013.01); *C07K 2317/76* (2013.01); *C07K 2317/92* (2013.01)

(58) Field of Classification Search
CPC C07K 16/2896; C07K 16/30; C07K 2317/24; C07K 2317/565; C07K 2317/76; C07K 2317/92; A61K 2039/505
See application file for complete search history.

(56) References Cited

U.S. PATENT DOCUMENTS

| 4,474,893 A | 10/1984 | Reading |
| 4,714,681 A | 12/1987 | Reading |
| 4,925,648 A | 5/1990 | Hansen |
| 5,573,920 A | 11/1996 | Randle |
| 5,601,819 A | 2/1997 | Wong |
| 5,714,350 A | 2/1998 | Co |
| 6,350,861 B1 | 2/2002 | Co |
| 2005/0154192 A1 | 7/2005 | Shirakawa |
| 2009/0092612 A1 | 4/2009 | Takayama |
| 2013/0143227 A1 | 6/2013 | Lin |
| 2013/0287777 A1 | 10/2013 | Duffy |

FOREIGN PATENT DOCUMENTS

| WO | WO 91/00360 | 1/1991 |
| WO | WO 92/05793 | 4/1992 |
| WO | WO 92/08802 | 5/1992 |
| WO | WO 93/17715 | 9/1993 |
| WO | WO 00/03016 | 1/2000 |
| WO | WO 2008/136774 | 11/2008 |
| WO | WO 2013/067055 | 5/2013 |
| WO | WO 2013/126810 | 8/2013 |
| WO | WO 2013/165894 | 11/2013 |

OTHER PUBLICATIONS

Paul, WE. Fundamental Immunology, 3rd ed. Raven Press, NY, Chap. 9, pp. 292-295, 1993.*
Rudikoff S. et al. Proc. Natl. Acad. Sci. USA, 79:1979-1983, 1982.*
Colman, PM. Research in Immunology, Elsevier, NY, 145(1):33-36, 1994.*
International Search Report and Written opinion issued in PCT/2015/36300 on Nov. 25, 2015.
Karlin et al., "Applications and statistics for multiple high-scoring segments in molecular sequences," Proc. Natl. Acad. Sci. USA, 90:5873-5877 (1993).
Schaffer et al., "Improving the accuracy of PSI-BLAST protein database searches with composition-based statistics and other refinements," Nucleic Acids Res., 29:2994-3005 (2001).

* cited by examiner

*Primary Examiner* — Robert Landsman
(74) *Attorney, Agent, or Firm* — Knobbe, Martens, Olson & Bear LLP

(57) ABSTRACT

Disclosed herein are anti-LGR4 antibodies for the treatment of cancer. Antibodies disclosed herein may bind LGR4 without disrupting LGR4-RSPO1 binding or signaling, and may disrupt LGR4 signaling through Wnt that is independent of RSPO1. Also disclosed are heavy and light chain polypeptide sequences for antibodies that bind LGR4, for example without disrupting LGR4-RSPO binding or signaling.

30 Claims, 11 Drawing Sheets

\* = significant by two-way t-test with multiple comparisons to MOPC

\* = significant by two-way t-test with multiple comparisons to MOPC

SEQUENCE LISTING

<160> NUMBER OF SEQ ID NOS: 19

<210> SEQ ID NO 1
<211> LENGTH: 5248
<212> TYPE: DNA
<213> ORGANISM: Homo sapiens
<220> FEATURE:
<221> NAME/KEY: misc_feature
<222> LOCATION: (0)...(0)
<223> OTHER INFORMATION: LGR4

<400> SEQUENCE: 1
gcgtgcaacc ctagaaggga aaaggacggg aagagattga gccgcggctg ggagacagcg     60
agccagagtc tgggtgtttg tgcgagagcc acggcggggg ctggggcgag tggccggcat    120
ggctgaaggc tgcgctctgc aaccttgaag agccgctgca ttgagaggcc agggacaggg    180

```
agaccggtgc gatggcagag cgcggccccc gccgctgcgc cgggccggcc cggctggcct    240
gagccgccgg aggagcgggg ctgcctctgc gcgtccatgg agcagcggga agggcgaaac    300
tccggagcgc cgcgtccctg cgccgctgcg gcggactgct gaaggggccg agcccgcgcg    360
gaccgccgag gaagagaccc ccgctccagc ccgcaggccg gctgcccggg ggcggcgggg    420
gacatcggag ggcagcggag cgagcagcgc cgcgggagag gccggcgcgg gaggcggccg    480
cagcaatgcc gggcccgcta gggctgctct gcttcctcgc cctggggctg ctcggctcgg    540
ccgggcccag cggcgcggcg ccgcctctct gcgcggcgcc ctgcagctgc gacggcgacc    600
gtcgggtgga ctgctccggg aaggggctga cggccgtgcc cgaggggctc agcgccttca    660
cccaagcgct ggatatcagt atgaacaaca ttactcagtt gccagaagat gcatttaaga    720
actttccttt tctagaagag ctacaattgg cgggcaacga cctttctttt atccacccaa    780
aggccttgtc tgggttgaaa gaactcaaag ttctaacgct ccagaataat cagttgaaaa    840
cagtacccag tgaagccatt cgagggctga gtgctttgca gtctttgcgt ttagatgcca    900
accatattac ctcagtcccc gaggacagtt ttgaaggact tgttcagtta cggcatctgt    960
ggctggatga caacagcttg acggaggtgc ctgtgcaccc cctcagcaat ctgcccaccc   1020
tacaggcgct gaccctggct ctcaacaaga tctcaagcat ccctgacttt gcatttacca   1080
acctttcaag cctggtagtt ctgcatcttc ataacaataa aattgaagc ctgagtcaac   1140 actgttttga tggactagat aacctggaga ccttagactt gaattataat aacttggggg   1200
aatttcctca ggctattaaa gcccttccta gccttaaaga gctaggattt catagtaatt   1260
ctatttctgt tatccctgat ggagcatttg atggtaatcc actcttaaga actatacatt   1320
tgtatgataa tcctctgtct tttgtgggga actcagcatt tcacaattta tctgatcttc   1380
attccctagt cattcgtggt gcaagcatgg tgcagcagtt ccccaatctt acaggaactg   1440
tccacctgga aagtctgact ttgacaggta caaagataag cagcatacct aataatttgt   1500
gtcaagaaca aaagatgctt aggactttgg acttgtctta caataatata agagaccttc   1560
caagttttaa tggttgccat gctctggaag aaatttcttt acagcgtaat caaatctacc   1620
aaataaagga aggcaccttt caaggcctga tatctctaag gattctagat ctgagtagaa   1680
acctgataca tgaaattcac agtagagctt ttgccacact tgggccaata actaacctag   1740
atgtaagttt caatgaatta acttcctttc ctacggaagg cctgaatggg ctaaatcaac   1800
tgaaacttgt gggcaacttc aagctgaaag aagccttagc agcaaaagac tttgttaacc   1860
tcaggtcttt atcagtacca tatgcttatc agtgctgtgc attttggggt tgtgactctt   1920
atgcaaattt aaacacagaa gataacagcc tccaggacca cagtgtggca caggagaaag   1980
gtactgctga tgcagcaaat gtcacaagca ctccttgaaaa tgaagaacat agtcaaataa   2040
ttatccattg tacaccttca acaggtgctt ttaagccctg tgaatattta ctgggaagct   2100
ggatgattcg tcttactgtg tggttcattt tcttggttgc attattttc aacctgcttg   2160 ttattttaac aacatttgca tcttgtacat cactgccttc gtccaaattg tttataggct   2220
tgatttctgt gtctaactta ttcatgggaa tctatactgg catcctaact tttcttgatg   2280
ctgtgtcctg gggcagattc gctgaatttg gcatttggtg ggaaactggc agtggctgca   2340
aagtagctgg gtttcttgca gttttctcct cagaaagtgc catatttta ttaatgctag   2400 caactgtcga aagaagctta tctgcaaaag atataatgaa aaatgggaag agcaatcatc   2460
tcaaacagtt ccgggttgct gccctttgg cttttcctagg tgctacagta gcaggctgtt   2520
```

-continued

```
ttcccctttt ccatagaggg gaatattctg catcacccct ttgtttgcca tttcctacag    2580
gtgaaacgcc atcattagga ttcactgtaa cgttagtgct attaaactca ctagcatttt    2640
tattaatggc cgttatctac actaagctat actgcaactt ggaaaaagag gacctctcag    2700
aaaactcaca atctagcatg attaagcatg tcgcttggct aatcttcacc aattgcatct    2760
ttttctgccc tgtggcgttt ttttcatttg caccattgat cactgcaatc tctatcagcc    2820
ccgaaataat gaagtctgtt actctgatat ttttccatt gcctgcttgc ctgaatccag     2880
tcctgtatgt tttcttcaac ccaaagttta agaagactg gaagttactg aagcgacgtg     2940
ttaccaagaa aagtggatca gtttcagttt ccatcagtag ccaaggtggt tgtctggaac    3000
aggatttcta ctacgactgt ggcatgtact cacatttgca gggcaacctg actgtttgcg    3060
actgctgcga atcgtttctt ttaacaaagc cagtatcatg caaacacttg ataaaatcac    3120
acagctgtcc tgcattggca gtggcttctt gccaaagacc tgagggctac tggtccgact    3180
gtggcacaca gtcggcccac tctgattatg cagatgaaga agattccttt gtctcagaca    3240
gttctgacca ggtgcaggcc tgtggacgag cctgcttcta ccagagtaga ggattcccctt   3300
tggtgcgcta tgcttacaat ctaccaagag ttaaagactg aactactgtg tgtgtaaccg    3360
tttcccccgt caaccaaaat cagtgtttat agagtgaacc ctattctcat ctttcatctg    3420
ggaagcactt ctgtaatcac tgcctggtgt cacttagaag aaggagaggt ggcagtttat    3480
ttctcaaacc agtcatttc aaagaacagg tgcctaaatt ataattggt gaaaaatgca     3540
atgtccaagc aatgtatgat ctgtttgaaa caaatatatg acttgaaaag gatcttaggt    3600
gtagtagagc aatataatgt tagttttttc tgatccataa gaagcaaatt tatacctatt    3660
tgtgtattaa gcacaagata aagaacagct gttaatattt tttaaaaatc tattttaaaa    3720
tgtgattttc tataactgaa gaaaatatct tgctaatttt acctaatgtt tcatccttaa    3780
tctcaggaca acttactgca gggccaaaaa agggactgtc ccagctagaa ctgtgagagt    3840
atacataggc attactttat tatgttttca cttgccatcc ttgacataag agaactataa    3900
attttgttta agcaatttat aaatctaaaa cctgaagatg ttttaaaac aatattaaca     3960
gctgttaggt taaaaaaata gctggacatt tgttttcagt cattatacat tgctttggtc    4020
caatcagtaa ttttttctta agtgttttgt gattacacta ctagaaaaaa agtaaaaggc    4080
taattgctgt gtgggtttag tcgatttggc taaactacta actaatgtgg gggtttaata    4140
gtatctgagg gatttggtgg cttcatgtaa tgttctcatt aatgaatact tcctaatatc    4200
gttggctcta ctaatatttt ccaatttgct gggatgtcac ctagcaatag cttggattat    4260
atagaaagta aactgtggtc aatacttgca tttaattaga cgaaacgggg agtaattatg    4320
acacgaagta cttatgttta tttcttagtg agctggatta tcttgaacct gtgctattaa    4380
atggaaattt ccatacatct tccccatact attttttata aaagagccta ttcaatagct    4440
cagaggttga actctggtta aacaagataa tatgttatta ataaaaatag aagaagaaag    4500
aataaagctt agtcctgtgt cttaaaaat taaaaatttt acttgattcc catctatggg     4560
ctttagacct attactgggt ggagtcttaa agttataatt gttcaatatg tttttttgaac   4620
agtgtgctaa atcaatagca aacccactgc catattagtt attctgaata tactaaaaaa    4680
atccagctag attgcagttt aataattaaa ctgtacatac tgtgcatata atgaattttt    4740
atcttatgta aattatttttt agaacacaag ttgggaaatg tggcttctgt tcatttcgtt   4800
taattaaagc tacctcctaa actatagtgg ctgccagtag cagactgtta aattgtggtt    4860
tatatacttt ttgcattgta aatagtcttt gttgtacatt gtcagtgtaa taaaaacaga    4920
```

-continued

```
atctttgtat atcaaaatca tgtagtttgt ataaaatgtg ggaaggattt atttacagtg    4980
tgttgtaatt ttgtaaggcc aactatttac aagttttaaa aattgctatc atgtatattt    5040
acacatctga taaatattaa atcataactt ggtaagaaac tcctaattaa aaggtttttt    5100
ccaaaattca ggttattgaa aactttccat tttattcatt taaaaactag aataacagat    5160
atataaaagt gttaatcttt gtgctatatg gtatgaaata caatattgta ctcagtgttt    5220
tgaattatta aagtttctag aaagcaaa                                       5248
```

<210> SEQ ID NO 2
<211> LENGTH: 951
<212> TYPE: PRT
<213> ORGANISM: Homo sapiens
<220> FEATURE:
<221> NAME/KEY: VARIANT
<222> LOCATION: (0)...(0)
<223> OTHER INFORMATION: LGR4

<400> SEQUENCE: 2

```
Met Pro Gly Pro Leu Gly Leu Leu Cys Phe Leu Ala Leu Gly Leu Leu
  1               5                  10                  15

Gly Ser Ala Gly Pro Ser Gly Ala Ala Pro Pro Leu Cys Ala Ala Pro
             20                  25                  30

Cys Ser Cys Asp Gly Asp Arg Arg Val Asp Cys Ser Gly Lys Gly Leu
         35                  40                  45

Thr Ala Val Pro Glu Gly Leu Ser Ala Phe Thr Gln Ala Leu Asp Ile
     50                  55                  60

Ser Met Asn Asn Ile Thr Gln Leu Pro Glu Asp Ala Phe Lys Asn Phe
 65                  70                  75                  80

Pro Phe Leu Glu Glu Leu Gln Leu Ala Gly Asn Asp Leu Ser Phe Ile
                 85                  90                  95

His Pro Lys Ala Leu Ser Gly Leu Lys Glu Leu Lys Val Leu Thr Leu
            100                 105                 110

Gln Asn Asn Gln Leu Lys Thr Val Pro Ser Glu Ala Ile Arg Gly Leu
        115                 120                 125

Ser Ala Leu Gln Ser Leu Arg Leu Asp Ala Asn His Ile Thr Ser Val
    130                 135                 140

Pro Glu Asp Ser Phe Glu Gly Leu Val Gln Leu Arg His Leu Trp Leu
145                 150                 155                 160

Asp Asp Asn Ser Leu Thr Glu Val Pro Val His Pro Leu Ser Asn Leu
                165                 170                 175

Pro Thr Leu Gln Ala Leu Thr Leu Ala Leu Asn Lys Ile Ser Ser Ile
            180                 185                 190

Pro Asp Phe Ala Phe Thr Asn Leu Ser Ser Leu Val Val Leu His Leu
        195                 200                 205

His Asn Asn Lys Ile Arg Ser Leu Ser Gln His Cys Phe Asp Gly Leu
    210                 215                 220

Asp Asn Leu Glu Thr Leu Asp Leu Asn Tyr Asn Asn Leu Gly Glu Phe
225                 230                 235                 240

Pro Gln Ala Ile Lys Ala Leu Pro Ser Leu Lys Glu Leu Gly Phe His
                245                 250                 255

Ser Asn Ser Ile Ser Val Ile Pro Asp Gly Ala Phe Asp Gly Asn Pro
            260                 265                 270

Leu Leu Arg Thr Ile His Leu Tyr Asp Asn Pro Leu Ser Phe Val Gly
        275                 280                 285
```

-continued

Asn Ser Ala Phe His Asn Leu Ser Asp Leu His Ser Leu Val Ile Arg
290                 295                 300

Gly Ala Ser Met Val Gln Gln Phe Pro Asn Leu Thr Gly Thr Val His
305                 310                 315                 320

Leu Glu Ser Leu Thr Leu Thr Gly Thr Lys Ile Ser Ser Ile Pro Asn
            325                 330                 335

Asn Leu Cys Gln Glu Gln Lys Met Leu Arg Thr Leu Asp Leu Ser Tyr
            340                 345                 350

Asn Asn Ile Arg Asp Leu Pro Ser Phe Asn Gly Cys His Ala Leu Glu
            355                 360                 365

Glu Ile Ser Leu Gln Arg Asn Gln Ile Tyr Gln Ile Lys Glu Gly Thr
370                 375                 380

Phe Gln Gly Leu Ile Ser Leu Arg Ile Leu Asp Leu Ser Arg Asn Leu
385                 390                 395                 400

Ile His Glu Ile His Ser Arg Ala Phe Ala Thr Leu Gly Pro Ile Thr
                405                 410                 415

Asn Leu Asp Val Ser Phe Asn Glu Leu Thr Ser Phe Pro Thr Glu Gly
            420                 425                 430

Leu Asn Gly Leu Asn Gln Leu Lys Leu Val Gly Asn Phe Lys Leu Lys
            435                 440                 445

Glu Ala Leu Ala Ala Lys Asp Phe Val Asn Leu Arg Ser Leu Ser Val
450                 455                 460

Pro Tyr Ala Tyr Gln Cys Cys Ala Phe Trp Gly Cys Asp Ser Tyr Ala
465                 470                 475                 480

Asn Leu Asn Thr Glu Asp Asn Ser Leu Gln Asp His Ser Val Ala Gln
                485                 490                 495

Glu Lys Gly Thr Ala Asp Ala Ala Asn Val Thr Ser Thr Leu Glu Asn
            500                 505                 510

Glu Glu His Ser Gln Ile Ile Ile His Cys Thr Pro Ser Thr Gly Ala
            515                 520                 525

Phe Lys Pro Cys Glu Tyr Leu Leu Gly Ser Trp Met Ile Arg Leu Thr
530                 535                 540

Val Trp Phe Ile Phe Leu Val Ala Leu Phe Phe Asn Leu Leu Val Ile
545                 550                 555                 560

Leu Thr Thr Phe Ala Ser Cys Thr Ser Leu Pro Ser Ser Lys Leu Phe
                565                 570                 575

Ile Gly Leu Ile Ser Val Ser Asn Leu Phe Met Gly Ile Tyr Thr Gly
            580                 585                 590

Ile Leu Thr Phe Leu Asp Ala Val Ser Trp Gly Arg Phe Ala Glu Phe
            595                 600                 605

Gly Ile Trp Trp Glu Thr Gly Ser Gly Cys Lys Val Ala Gly Phe Leu
610                 615                 620

Ala Val Phe Ser Ser Glu Ser Ala Ile Phe Leu Leu Met Leu Ala Thr
625                 630                 635                 640

Val Glu Arg Ser Leu Ser Ala Lys Asp Ile Met Lys Asn Gly Lys Ser
            645                 650                 655

Asn His Leu Lys Gln Phe Arg Val Ala Ala Leu Leu Ala Phe Leu Gly
            660                 665                 670

Ala Thr Val Ala Gly Cys Phe Pro Leu Phe His Arg Gly Glu Tyr Ser
            675                 680                 685

Ala Ser Pro Leu Cys Leu Pro Phe Pro Thr Gly Glu Thr Pro Ser Leu
690                 695                 700

Gly Phe Thr Val Thr Leu Val Leu Leu Asn Ser Leu Ala Phe Leu Leu

```
                705                 710                 715                 720
Met Ala Val Ile Tyr Thr Lys Leu Tyr Cys Asn Leu Glu Lys Glu Asp
                    725                 730                 735

Leu Ser Glu Asn Ser Gln Ser Ser Met Ile Lys His Val Ala Trp Leu
                740                 745                 750

Ile Phe Thr Asn Cys Ile Phe Phe Cys Pro Val Ala Phe Ser Phe
                755                 760                 765

Ala Pro Leu Ile Thr Ala Ile Ser Ile Ser Pro Glu Ile Met Lys Ser
            770                 775                 780

Val Thr Leu Ile Phe Phe Pro Leu Pro Ala Cys Leu Asn Pro Val Leu
785                 790                 795                 800

Tyr Val Phe Phe Asn Pro Lys Phe Lys Glu Asp Trp Lys Leu Leu Lys
                    805                 810                 815

Arg Arg Val Thr Lys Lys Ser Gly Ser Val Ser Val Ser Ile Ser Ser
                820                 825                 830

Gln Gly Gly Cys Leu Glu Gln Asp Phe Tyr Tyr Asp Cys Gly Met Tyr
                    835                 840                 845

Ser His Leu Gln Gly Asn Leu Thr Val Cys Asp Cys Cys Glu Ser Phe
            850                 855                 860

Leu Leu Thr Lys Pro Val Ser Cys Lys His Leu Ile Lys Ser His Ser
865                 870                 875                 880

Cys Pro Ala Leu Ala Val Ala Ser Cys Gln Arg Pro Glu Gly Tyr Trp
                    885                 890                 895

Ser Asp Cys Gly Thr Gln Ser Ala His Ser Asp Tyr Ala Asp Glu Glu
                    900                 905                 910

Asp Ser Phe Val Ser Asp Ser Ser Asp Gln Val Gln Ala Cys Gly Arg
                915                 920                 925

Ala Cys Phe Tyr Gln Ser Arg Gly Phe Pro Leu Val Arg Tyr Ala Tyr
                    930                 935                 940

Asn Leu Pro Arg Val Lys Asp
945                 950

<210> SEQ ID NO 3
<211> LENGTH: 357
<212> TYPE: DNA
<213> ORGANISM: Rattus norvegicus
<220> FEATURE:
<221> NAME/KEY: misc_feature
<222> LOCATION: (0)...(0)
<223> OTHER INFORMATION: Mouse antibody to human LGR4, heavy chain

<400> SEQUENCE: 3
caggtgcagc tgcagcagtc aggggctgaa ctggtgaagc ctgggtcctc agtgaaaatt      60
tcctgcaagg cttctggcta caccttcacc agttacttta tacactggat aaaacagcag    120
cctggaaatg ccttgagtg gattgggtgg atttatcctg agatggtga tacagaatat    180 aatcaaaagt tcaatgggaa ggcaacattc attgcagaca atcctccag tacagccgat    240 atgcagctca acagcctgac atctgaggac tctgcagtct atttctgtgc aagatcgaag    300
tcggcgtaca attggtttgc ctactgggcc aaggcactc tggtcactgt ctcttca       357

<210> SEQ ID NO 4
<211> LENGTH: 318
<212> TYPE: DNA
<213> ORGANISM: Rattus norvegicus
<220> FEATURE:
<221> NAME/KEY: misc_feature
<222> LOCATION: (0)...(0)
```

<223> OTHER INFORMATION: Mouse antibody to human LGR4, light chain

<400> SEQUENCE: 4

```
gacatccaga tgacccagtc tcctccagtc ctgtctgcat ctgtgggaga cagagtcact      60
ctcagctgca aagcaagtca gaatattaat aagaacttag actggtatca tcaaaagcat    120
ggagaagcgc caaaactcct gatatattat acaaacaatt tgcaaacggg catcccatca    180
aggttcagtg gcagtggatc tggtacagat tacacactca tcatcagcag cctgcagcct    240
gaagatgttg ccacatatta ctgctatcag tataacagtg ggcccacgtt tggaactggg    300
accaagctgg aactgaaa                                                  318
```

<210> SEQ ID NO 5
<211> LENGTH: 119
<212> TYPE: PRT
<213> ORGANISM: Rattus norvegicus
<220> FEATURE:
<221> NAME/KEY: VARIANT
<222> LOCATION: (0)...(0)
<223> OTHER INFORMATION: Mouse antibody to human LGR4, heavy chain

<400> SEQUENCE: 5

```
Gln Val Gln Leu Gln Gln Ser Gly Ala Glu Leu Val Lys Pro Gly Ser
  1               5                  10                  15

Ser Val Lys Ile Ser Cys Lys Ala Ser Gly Tyr Thr Phe Thr Ser Tyr
             20                  25                  30

Phe Ile His Trp Ile Lys Gln Gln Pro Gly Asn Gly Leu Glu Trp Ile
         35                  40                  45

Gly Trp Ile Tyr Pro Gly Asp Gly Asp Thr Glu Tyr Asn Gln Lys Phe
     50                  55                  60

Asn Gly Lys Ala Thr Phe Ile Ala Asp Lys Ser Ser Thr Ala Asp
 65                  70                  75                  80

Met Gln Leu Asn Ser Leu Thr Ser Glu Asp Ser Ala Val Tyr Phe Cys
                 85                  90                  95

Ala Arg Ser Lys Ser Ala Tyr Asn Trp Phe Ala Tyr Trp Gly Gln Gly
            100                 105                 110

Thr Leu Val Thr Val Ser Ser
        115
```

<210> SEQ ID NO 6
<211> LENGTH: 106
<212> TYPE: PRT
<213> ORGANISM: Rattus norvegicus
<220> FEATURE:
<221> NAME/KEY: VARIANT
<222> LOCATION: (0)...(0)
<223> OTHER INFORMATION: Mouse antibody to human LGR4, light chain

<400> SEQUENCE: 6

```
Asp Ile Gln Met Thr Gln Ser Pro Pro Val Leu Ser Ala Ser Val Gly
  1               5                  10                  15

Asp Arg Val Thr Leu Ser Cys Lys Ala Ser Gln Asn Ile Asn Lys Asn
             20                  25                  30

Leu Asp Trp Tyr His Gln Lys His Gly Glu Ala Pro Lys Leu Leu Ile
         35                  40                  45

Tyr Tyr Thr Asn Asn Leu Gln Thr Gly Ile Pro Ser Arg Phe Ser Gly
     50                  55                  60

Ser Gly Ser Gly Thr Asp Tyr Thr Leu Ile Ile Ser Ser Leu Gln Pro
 65                  70                  75                  80
```

Glu Asp Val Ala Thr Tyr Tyr Cys Tyr Gln Tyr Asn Ser Gly Pro Thr
                85                  90                  95

Phe Gly Thr Gly Thr Lys Leu Glu Leu Lys
        100                 105

<210> SEQ ID NO 7
<211> LENGTH: 357
<212> TYPE: DNA
<213> ORGANISM: Rattus norvegicus
<220> FEATURE:
<221> NAME/KEY: misc_feature
<222> LOCATION: (0)...(0)
<223> OTHER INFORMATION: Mouse antibody to human LGR4, heavy chain

<400> SEQUENCE: 7
caggtacagc tgcagcaatc tggggctgaa ctggtgaagc ctgggtcctc agtgaaaatt      60
tcctgcaagg cttctggcta caccttcacc agtaacttta tgcactggat aaaacagcag     120
cctggaaatg gccctgagtg gattgggtgg atttatcctg agatggtga tacagagtac      180 aatcaaaagt tcaatgggaa ggcaacactc attgcagaca atcctccac cacagcctat      240 atgcagctca ggagcctgac atctgaggac tctgcagtct atttctgtgc aagaggcaat     300
tcgggttaca attggtttgc gtactggggc caaggcactc tggtcactgt ctcttca       357

<210> SEQ ID NO 8
<211> LENGTH: 318
<212> TYPE: DNA
<213> ORGANISM: Rattus norvegicus
<220> FEATURE:
<221> NAME/KEY: misc_feature
<222> LOCATION: (0)...(0)
<223> OTHER INFORMATION: Mouse antibody to human LGR4, light chain

<400> SEQUENCE: 8
gacatccaga tgacccagtc tcctccagtc ctgtctgcat ctgtgggaga cagagtcact      60
ctcagctgca aagcaagtca gaatattaat aagaacttag actggtatca gcaaaagcat     120
ggagaagctc caaggctcct gatatattat acaaacaatt tgcaaacggg catcccatca     180
aggttcagtg gcagtggatc tggtaccgat tacacactca ccatcagcag cctgcagcct     240
gaagatgttg ccacatattt ctgctatcag tataagagtg gaacacgtt tggagctggg      300 accaagctgg aactgaaa                                                   318

<210> SEQ ID NO 9
<211> LENGTH: 119
<212> TYPE: PRT
<213> ORGANISM: Rattus norvegicus
<220> FEATURE:
<221> NAME/KEY: VARIANT
<222> LOCATION: (0)...(0)
<223> OTHER INFORMATION: Mouse antibody to human LGR4, light chain

<400> SEQUENCE: 9

Gln Val Gln Leu Gln Gln Ser Gly Ala Glu Leu Val Lys Pro Gly Ser
 1               5                   10                  15

Ser Val Lys Ile Ser Cys Lys Ala Ser Gly Tyr Thr Phe Thr Ser Asn
                20                  25                  30

Phe Met His Trp Ile Lys Gln Gln Pro Gly Asn Gly Pro Glu Trp Ile
            35                  40                  45

Gly Trp Ile Tyr Pro Gly Asp Gly Asp Thr Glu Tyr Asn Gln Lys Phe
        50                  55                  60

Asn Gly Lys Ala Thr Leu Ile Ala Asp Lys Ser Ser Thr Thr Ala Tyr

```
                65                  70                  75                  80
Met Gln Leu Arg Ser Leu Thr Ser Glu Asp Ser Ala Val Tyr Phe Cys
                    85                  90                  95

Ala Arg Gly Asn Ser Gly Tyr Asn Trp Phe Ala Tyr Trp Gly Gln Gly
                100                 105                 110

Thr Leu Val Thr Val Ser Ser
        115

<210> SEQ ID NO 10
<211> LENGTH: 106
<212> TYPE: PRT
<213> ORGANISM: Rattus norvegicus
<220> FEATURE:
<221> NAME/KEY: VARIANT
<222> LOCATION: (0)...(0)
<223> OTHER INFORMATION: Mouse antibody to human LGR4, light chain

<400> SEQUENCE: 10

Asp Ile Gln Met Thr Gln Ser Pro Pro Val Leu Ser Ala Ser Val Gly
 1               5                  10                  15

Asp Arg Val Thr Leu Ser Cys Lys Ala Ser Gln Asn Ile Asn Lys Asn
                20                  25                  30

Leu Asp Trp Tyr Gln Gln Lys His Gly Glu Ala Pro Arg Leu Leu Ile
            35                  40                  45

Tyr Tyr Thr Asn Asn Leu Gln Thr Gly Ile Pro Ser Arg Phe Ser Gly
 50                  55                  60

Ser Gly Ser Gly Thr Asp Tyr Thr Leu Thr Ile Ser Ser Leu Gln Pro
65                  70                  75                  80

Glu Asp Val Ala Thr Tyr Phe Cys Tyr Gln Tyr Lys Ser Gly Asn Thr
                85                  90                  95

Phe Gly Ala Gly Thr Lys Leu Glu Leu Lys
                100                 105

<210> SEQ ID NO 11
<211> LENGTH: 106
<212> TYPE: PRT
<213> ORGANISM: Artificial Sequence
<220> FEATURE:
<223> OTHER INFORMATION: Recombinant/artificial light chain for
      anti-LGR4 antibody.

<400> SEQUENCE: 11

Glu Ile Val Met Thr Gln Ser Pro Ala Thr Leu Ser Val Ser Pro Gly
 1               5                  10                  15

Glu Arg Ala Thr Leu Ser Cys Lys Ala Ser Gln Asn Ile Asn Lys Asn
                20                  25                  30

Leu Asp Trp Tyr Gln Gln Lys Pro Gly Gln Ala Pro Arg Leu Leu Ile
            35                  40                  45

Tyr Tyr Thr Asn Asn Leu Gln Thr Gly Ile Pro Ala Arg Phe Ser Gly
 50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Tyr Gln Tyr Lys Ser Gly Asn Thr
                85                  90                  95

Phe Gly Gln Gly Thr Lys Leu Glu Ile Lys
                100                 105

<210> SEQ ID NO 12
<211> LENGTH: 119
```

```
<212> TYPE: PRT
<213> ORGANISM: Artificial Sequence
<220> FEATURE:
<223> OTHER INFORMATION: Recombinant/artificial heavy chain for
      anti-LGR4 antibody.

<400> SEQUENCE: 12
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Asn
            20                  25                  30

Phe Met His Trp Val Arg Gln Ala Pro Gly Gln Gly Leu Glu Trp Ile
        35                  40                  45

Gly Trp Ile Tyr Pro Gly Asp Gly Asp Thr Glu Tyr Asn Gln Lys Phe
    50                  55                  60

Asn Gly Lys Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Asn Ser Gly Tyr Asn Trp Phe Ala Tyr Trp Gly Gln Gly
            100                 105                 110

Thr Thr Val Thr Val Ser Ser
        115

```
<210> SEQ ID NO 13
<211> LENGTH: 119
<212> TYPE: PRT
<213> ORGANISM: Artificial Sequence
<220> FEATURE:
<223> OTHER INFORMATION: Recombinant/artificial heavy chain for
      anti-LGR4 antibody.

<400> SEQUENCE: 13
```

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Ser Asn
            20                  25                  30

Phe Met His Trp Val Arg Gln Met Pro Gly Lys Gly Leu Glu Trp Ile
        35                  40                  45

Gly Trp Ile Tyr Pro Gly Asp Gly Asp Thr Glu Tyr Asn Gln Lys Phe
    50                  55                  60

Asn Gly Lys Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Asn Ser Gly Tyr Asn Trp Phe Ala Tyr Trp Gly Gln Gly
            100                 105                 110

Thr Thr Val Thr Val Ser Ser
        115

```
<210> SEQ ID NO 14
<211> LENGTH: 12
<212> TYPE: PRT
<213> ORGANISM: Rattus norvegicus
<220> FEATURE:
<221> NAME/KEY: VARIANT
<222> LOCATION: (0)...(0)
<223> OTHER INFORMATION: Complementary determining region for mouse
      anti-LGR antibody

<400> SEQUENCE: 14
```

```
Lys Ala Ser Gln Asn Ile Asn Lys Asn Leu Asp Trp
 1               5                  10

<210> SEQ ID NO 15
<211> LENGTH: 11
<212> TYPE: PRT
<213> ORGANISM: Rattus norvegicus
<220> FEATURE:
<221> NAME/KEY: VARIANT
<222> LOCATION: (0)...(0)
<223> OTHER INFORMATION: Complementary determining region for mouse
      anti-LGR antibody

<400> SEQUENCE: 15

Leu Leu Ile Tyr Tyr Thr Asn Asn Leu Gln Thr
 1               5                  10

<210> SEQ ID NO 16
<211> LENGTH: 8
<212> TYPE: PRT
<213> ORGANISM: Rattus norvegicus
<220> FEATURE:
<221> NAME/KEY: VARIANT
<222> LOCATION: (0)...(0)
<223> OTHER INFORMATION: Complementary determining region for mouse
      anti-LGR antibody

<400> SEQUENCE: 16

Tyr Gln Tyr Lys Ser Gly Asn Thr
 1               5

<210> SEQ ID NO 17
<211> LENGTH: 10
<212> TYPE: PRT
<213> ORGANISM: Rattus norvegicus
<220> FEATURE:
<221> NAME/KEY: VARIANT
<222> LOCATION: (0)...(0)
<223> OTHER INFORMATION: Complementary determining region for mouse
      anti-LGR antibody

<400> SEQUENCE: 17

Gly Tyr Thr Phe Thr Ser Asn Phe Met His
 1               5                  10

<210> SEQ ID NO 18
<211> LENGTH: 20
<212> TYPE: PRT
<213> ORGANISM: Rattus norvegicus
<220> FEATURE:
<221> NAME/KEY: VARIANT
<222> LOCATION: (0)...(0)
<223> OTHER INFORMATION: Complementary determining region for mouse
      anti-LGR antibody

<400> SEQUENCE: 18

Trp Ile Gly Trp Ile Tyr Pro Gly Asp Gly Asp Thr Glu Tyr Asn Gln
 1               5                  10                  15

Lys Phe Asn Gly
            20

<210> SEQ ID NO 19
<211> LENGTH: 12
<212> TYPE: PRT
<213> ORGANISM: Rattus norvegicus
<220> FEATURE:
<221> NAME/KEY: VARIANT
<222> LOCATION: (0)...(0)
```

```
<223> OTHER INFORMATION: Complementary determining region for mouse
      anti-LGR antibody

<400> SEQUENCE: 19

Ala Arg Gly Asn Ser Gly Tyr Asn Trp Phe Ala Tyr
1               5                   10
```

ANTIBODIES THAT BIND LGR4, THEIR USE IN INHIBITING NEOPLASTIC CELLS AND IN TREATING TUMORS

CROSS-REFERENCE TO RELATED APPLICATIONS

This application claims the benefit of U.S. Prov. App. No. 62/015,980 filed Jun. 23, 2014, which is incorporated by reference herein in its entirety.

FIELD OF THE INVENTION

The present invention relates generally to the field of cancer biology. More particularly, embodiments are drawn to murine and humanized antibodies against LGR4 and uses of such antibodies. Several embodiments relate to monoclonal murine, humanized, or fully human antibodies against LGR4, hybridomas or other cell lines expressing such antibodies, nucleic acids and vectors comprising nucleic acids encoding for such antibodies, and methods of blocking cancer stem cell growth with such antibodies.

REFERENCE TO SEQUENCE LISTING

The present application is being filed along with a Sequence Listing in electronic format. The Sequence Listing is provided as a file entitled BIONO012ASUBSEQLIST, created Oct. 22, 2015, which is approximately 26 KB in size. The information in the electronic format of the Sequence Listing is incorporated herein by reference in its entirety.

BACKGROUND OF THE INVENTION

Leucine-rich repeat containing G-protein-coupled receptor 4 (LGR4), also known as GPR48 and BNMD17, belongs to the leucine-rich repeat containing G-protein-coupled receptor (LGR)/G-Protein-coupled Receptor (GPR) protein family of receptor proteins that are structurally similar to glycoprotein hormone receptors. LGRs are divided into three subgroups: (1) glycoprotein hormone receptors including thyroid-stimulating hormone (TSH) receptor, follicle-stimulating hormone (FSH) receptor, and luteinizing hormone (LH) receptor; (2) relaxin receptors LGR7 and LGR8; and (3) LGR4, LGR5, and LGR6.

SUMMARY OF THE INVENTION

Some embodiments of the methods and compositions provided herein include an antigen binding protein or fragment thereof that specifically binds to a LGR4 polypeptide. In some embodiments the antigen binding protein or fragment thereof has an EC50 for LGR4 binding less than 2 nM. In some embodiments the antigen binding protein or fragment thereof has activity to inhibit growth of a neoplastic cell in vivo.

Some embodiments include a polypeptide having at least 90% identity with a complementary determining region (CDR) polypeptide selected from the group consisting of SEQ ID NO.s:14-19.

Some embodiments include a complementary determining region (CDR) polypeptide selected from the group consisting of SEQ ID NO.s:14-19.

Some embodiments include a VL polypeptide having at least 90% identity with a VL complementary determining region (CDR) polypeptide selected from the group consisting of SEQ ID NO.s:14-16, and a VH polypeptide having at least 90% identity with a VH complementary determining region (CDR) polypeptide selected from the group consisting of SEQ ID NO.s:17-19.

Some embodiments include a VL complementary determining region (CDR) polypeptide selected from the group consisting of SEQ ID NO.s:14-16, and a VH complementary determining region (CDR) polypeptide selected from the group consisting of SEQ ID NO.s:17-19.

Some embodiments include a polypeptide having at least 90% identity with a humanized polypeptide selected from the group consisting of SEQ ID NO.s:11-13.

Some embodiments include a humanized polypeptide selected from the group consisting of SEQ ID NO.s:11-13.

Some embodiments include a VL polypeptide having at least 90% identity with SEQ ID NO:11, and a VH polypeptide having at least 90% identity with a VH polypeptide selected from the group consisting of SEQ ID NO.s:12 and 13.

Some embodiments include a VL polypeptide comprising SEQ ID NO:11, and a VH polypeptide selected from the group consisting of SEQ ID NO.s:12 and 13.

Some embodiments include a polypeptide having at least 90% identity with a polypeptide selected from the group consisting of SEQ ID NO.s:05, 06, 09, and 10.

Some embodiments include a polypeptide selected from the group consisting of SEQ ID NO.s: 05, 06, 09, and 10.

In some embodiments, the antigen binding protein or fragment thereof has an EC50 for LGR4 binding less than 1 nM. In some embodiments, the antigen binding protein or fragment thereof has an EC50 for LGR4 binding less than 0.5 nM. In some embodiments, the antigen binding protein or fragment thereof has an EC50 for LGR4 binding about 500 pM.

In some embodiments, the antigen binding protein or fragment thereof has a $K_D$ for LGR4 binding less than 1.5 nM. In some embodiments, the antigen binding protein or fragment thereof has a $K_D$ for LGR4 binding less than 0.5 nM. In some embodiments, the antigen binding protein or fragment thereof has a $K_D$ for LGR4 binding about 0.47 nM.

In some embodiments, the antigen binding protein or fragment thereof lacks activity to inhibit binding between LGR4 and a R-spondin protein. In some embodiments, the antigen binding protein or fragment thereof lacks activity to inhibit binding between LGR4 and a R-spondin-4 protein.

In some embodiments, the neoplastic cell is selected from the group consisting of lung tumor cell, breast tumor cell, ovarian tumor cell, colon tumor cell, and pancreatic tumor cell. In some embodiments, the neoplastic cell is a breast cancer cell. In some embodiments, the neoplastic cell is a triple negative breast cancer cell. In some embodiments, the neoplastic cell is a colon cancer cell. In some embodiments, the neoplastic cell is a colon cancer cell having a mutation in a gene selected from the group consisting of K-Ras, P13K, PTEN, p53 and APC. In some embodiments, the neoplastic cell is a small cell lung cancer cell.

In some embodiments, the neoplastic cell is a cancer stem cell. In some embodiments, the cancer stem cell comprises CD44+ and CD44+/CD24−.

In some embodiments, the antigen binding protein or fragment thereof has activity to inhibit growth of a tumor comprising the neoplastic cell.

In some embodiments, the antigen binding protein or fragment thereof has activity to reduce the frequency of cancer stem cells in a tumor.

In some embodiments, the antigen binding protein or fragment thereof has activity to inhibit growth of a tumor comprising the neoplastic cell by at least 25% compared to the growth of a tumor not contacted with the antigen binding protein or fragment thereof. In some embodiments, the antigen binding protein or fragment thereof has activity to inhibit growth of a tumor comprising the neoplastic cell by at least 50% compared to the growth of a tumor not contacted with the antigen binding protein or fragment thereof.

In some embodiments, the antigen binding protein or fragment thereof is a monoclonal antibody. In some embodiments, the monoclonal antibody is selected from the group consisting of 1C5 and 8F3. In some embodiments, the antigen binding protein or fragment thereof is a humanized monoclonal antibody. In some embodiments, the humanized monoclonal antibody is selected from the group consisting of 1C5HE and 1C5HG.

In some embodiments, the neoplastic cell is human.

Some embodiments of the methods and compositions provided herein include an isolated nucleic acid encoding any one of the foregoing the antigen binding proteins or fragment thereof. Some embodiments of the methods and compositions provided herein include a vector comprising the isolated nucleic acid. Some embodiments of the methods and compositions provided herein include a cell comprising the vector. Some embodiments of the methods and compositions provided herein include a method of preparing the antigen binding protein or fragment thereof comprising culturing the cell.

Some embodiments of the methods and compositions provided herein include a pharmaceutical composition comprising the antigen binding protein or fragment thereof a pharmaceutically acceptable carrier.

Some embodiments of the methods and compositions provided herein include a method of inhibiting growth of a neoplastic cell comprising contacting the cell with the antigen binding protein or fragment thereof.

In some embodiments, the neoplastic cell is selected from the group consisting of lung tumor cell, breast tumor cell, ovarian tumor cell, colon tumor cell, and pancreatic tumor cell. In some embodiments, the neoplastic cell is a breast cancer cell. In some embodiments, the neoplastic cell is a triple negative breast cancer cell. In some embodiments, the neoplastic cell is a colon cancer cell. In some embodiments, the neoplastic cell is a colon cancer cell having a mutation in a gene selected from the group consisting of K-Ras, P13K, PTEN, p53 and APC. In some embodiments, the neoplastic cell is a small cell lung cancer cell.

In some embodiments, the neoplastic cell is a cancer stem cell. In some embodiments, the cancer stem cell comprises CD44+ and CD44+/CD24−.

In some embodiments, the neoplastic cell is human.

Some embodiments of the methods and compositions provided herein include a method of ameliorating a tumor comprising administering to a subject in need thereof an effective amount of the antigen binding protein or fragment thereof.

In some embodiments, the tumor is selected from the group consisting of lung tumor, breast tumor, ovarian tumor, colon tumor, and pancreatic tumor. In some embodiments, the tumor is a breast cancer tumor. In some embodiments, the tumor is a triple negative breast cancer tumor. In some embodiments, the tumor is a colon cancer tumor. In some embodiments, the tumor is a colon cancer tumor comprising a mutation in a gene selected from the group consisting of K-Ras, P13K, PTEN, p53 and APC. In some embodiments, the tumor is a small cell lung cancer tumor.

In some embodiments, the tumor comprises a population of cancer stem cells. In some embodiments, the cancer stem cells comprise CD44+ and CD44+/CD24−.

In some embodiments, the antigen binding protein or fragment thereof inhibits growth of the tumor.

In some embodiments, the antigen binding protein or fragment thereof reduces the frequency of cancer stem cells in a tumor.

In some embodiments, the antigen binding protein or fragment thereof inhibits growth of the tumor by at least 25% compared to the growth of a tumor not contacted with the antigen binding protein or fragment thereof. In some embodiments, the antigen binding protein or fragment thereof inhibits growth of the tumor by at least 50% compared to the growth of a tumor not contacted with the antigen binding protein or fragment thereof.

In some embodiments, the subject is human.

10A) and CD44+/CD24− (FIG. 10B) subpopulations in the 1C5 treated tumors compared to PBS or MOPC.

Figure 11:
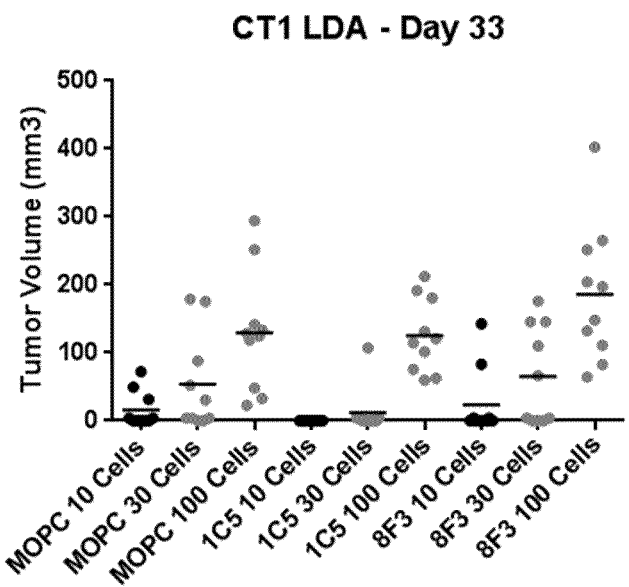

FIG. 11 is a graph showing treatment with anti-LGR4 antibodies 1C5 and 8F3 reduced tumorgenicity of colorectal PDX tumor cells re-implanted into naïve mice as compared to cells isolated from mice treated with control antibody MOPC alone.

Figures 12A, 12B:
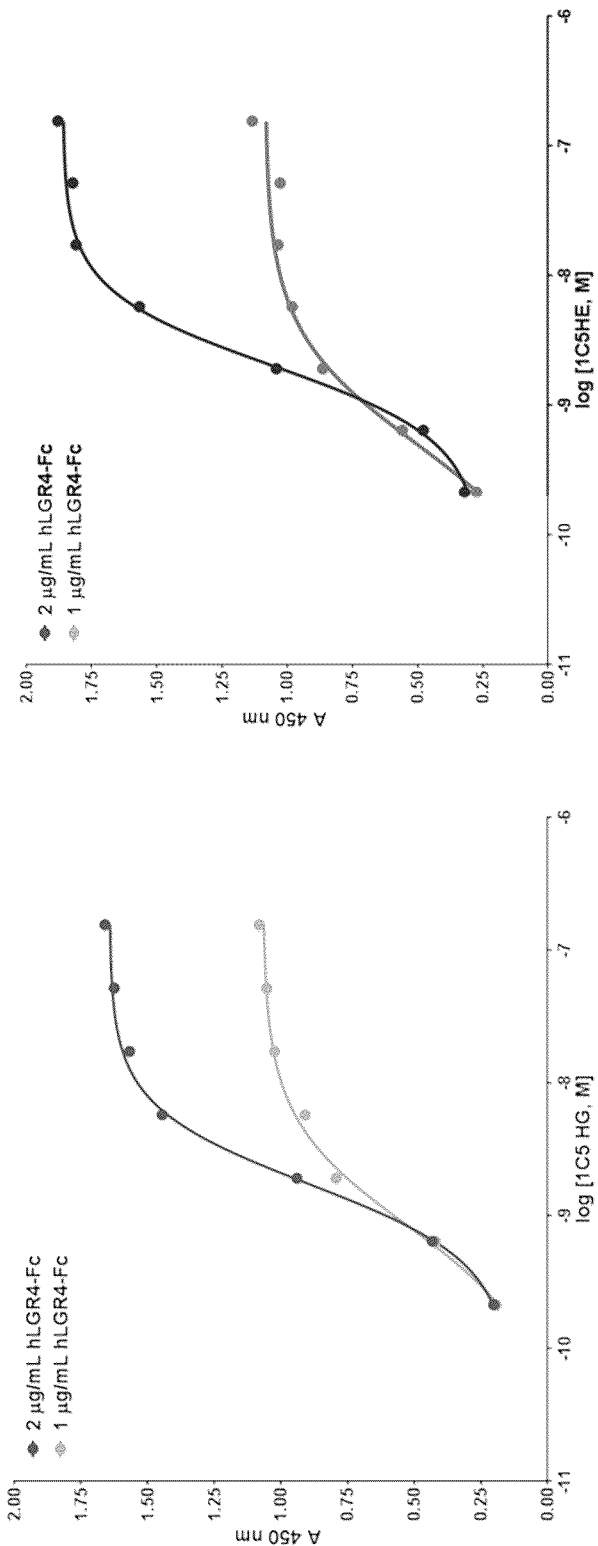

FIGS. 12A, and 12B depicts graphs for binding of the 1C5HG (FIG. 12A) and 1C5HE (FIG. 12B) and to human LGR4.

Figure 13:
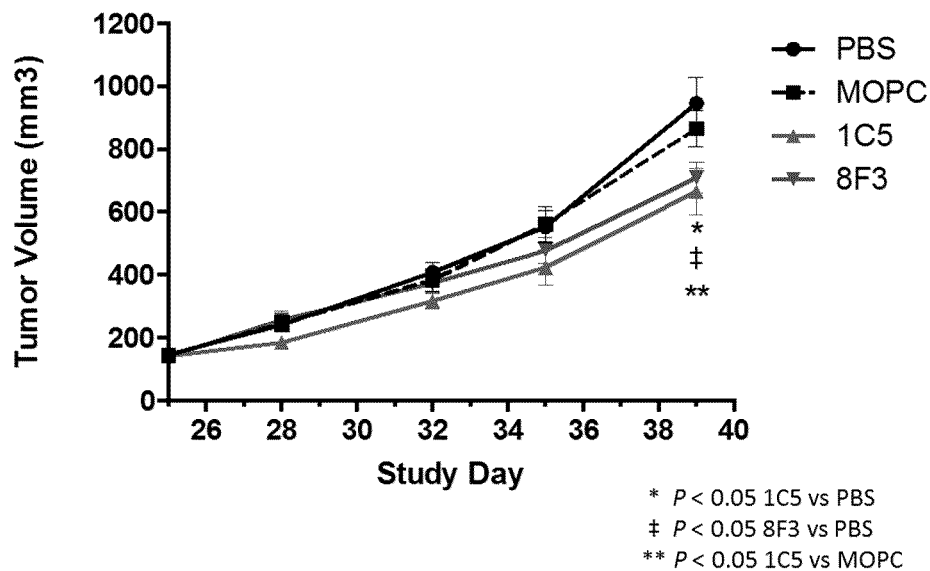

FIG. 13 is a line graph showing triple negative breast cancer tumor volume over time in xenograft models treated with anti-LGR4 antibodies.

Figure 14:
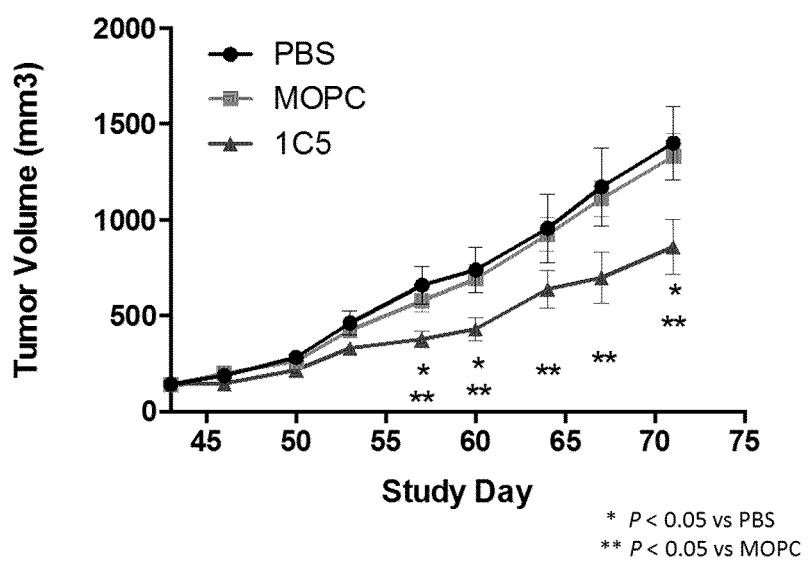

FIG. 14 is a line graph showing small cell lung cancer tumor volume over time in xenograft models treated with anti-LGR4 antibodies.

DETAILED DESCRIPTION

Several embodiments of the present application are drawn to murine or humanized monoclonal antibodies that specifically bind to LGR4 and methods of inhibiting cancer stem cell growth with such antibodies. In some embodiments, the antibodies specifically bind LGR4 but do not inhibit R-Spondin (R-Spo) binding to LGR4.

Another embodiment is antibodies that bind LGR4 and also inhibit LGR4 signaling through the Wnt pathway. In some embodiments, these antibodies may inhibit LGR4 signaling through the Wnt pathway, and be independent of RSpo signaling.

Other embodiments include methods of using the antibodies described above to inhibit LGR4 or R-Spo signaling in a cell or tissue.

The specific expression of LGR4 on cancer stem cells (CSCs) provides an opportunity to target CSCs selectively and effectively. LGR4 is over expressed in breast, lung and a number of other solid tumors, compared to normal tissues, thereby providing a wide therapeutic window to target CSCs in CRC, pancreatic, breast, ovarian, lung, and gastric cancer.

CSCs are believed to responsible for the high incidence of tumor recurrence in many cancer patients treated with surgery and standard of care chemotherapy. For example, CD44+ CSCs from breast cancer patients were found to be enriched following chemotherapy, and that high levels of CSCs correlated with poor clinical response to chemotherapy. Similarly, in metastatic CRC, LGR4 expression was upregulated in damaged liver following chemotherapy, suggesting that increased LGR4 CSCs in response to chemotherapy initiate and/or acerbate metastatic disease.

Anti-LGR4 Antibodies

As used herein, the term "antibody" includes, but is not limited to, synthetic antibodies, monoclonal antibodies, recombinantly produced antibodies, intrabodies, multispecific antibodies (including bi-specific antibodies), human antibodies, humanized antibodies, chimeric antibodies, synthetic antibodies, single-chain Fvs (scFv), Fab fragments, F(ab') fragments, disulfide-linked Fvs (sdFv) (including bi-specific sdFvs), and anti-idiotypic (anti-Id) antibodies, and epitope-binding fragments of any of the above. The antibodies of several embodiments provided herein may be monospecific, bispecific, trispecific or of greater multispecificity. Multispecific antibodies may be specific for different epitopes of a polypeptide or may be specific for both a polypeptide as well as for a heterologous epitope, such as a heterologous polypeptide or solid support material. See, e.g., PCT publications WO 93/17715; WO 92/08802; WO91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et al., J. Immunol. 148: 1547-1553 (1992); each of which is incorporated herein by reference in its entirety.

As used herein, LGR4 includes, but is not limited to, human LGR4 including the polypeptide of NCBI Accession No. NP_060960.2, or fragments thereof, which is encoded by the coding nucleotide sequence within NM_018490.2, or fragments thereof. The amino acid sequence and entire entry of NCBI Accession No. NP_060960.2 and nucleotide sequence and entire entry of NM_018490.2 are fully incorporated by reference in their entireties. Examples of LGR4 fragments contemplated herein include the LGR4 ectodomain, transmembrane domain, or intracellular domain and portions thereof.

Several embodiments relate to a hybridoma that produces the light chain and/or the heavy chain of an anti-LGR4 antibody, including the anti-LGR4 antibodies designated as 8F3 and 1C5 produced and described in the Examples below.

Some embodiments are drawn to a nucleic acid molecule encoding the light chain or the heavy chain of an anti-LGR4 antibodies, including any one of the anti-LGR4 antibodies designated as 8F3 and 1C5 produced and described in the Examples below.

Various embodiments are directed to a vector comprising a nucleic acid molecule or molecules encoding a light chain and/or a heavy chain of an anti-LGR4 antibody, including any one of the anti-LGR4 antibodies designated as 8F3 and 1C5 produced and described in the Examples below.

In various embodiments, the glycosylation of the antibodies can be modified. For example, an aglycosylated antibody can be made (i.e., the antibody lacks glycosylation). Glycosylation can be altered to, for example, increase the affinity of the antibody for a target antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861; each of which is incorporated herein by reference in its entirety.

In several embodiments, the antibodies specifically bind a polypeptide comprising or consisting of a LGR4 polypeptide having at least 60% identity, or at least 70% identity, or at least 80% identity, at least 85% identity, at least 90% identity, at least 95% identity, or at least at least 97% identity, or at least 99% identity, or 100% identity to the human LGR4 polypeptide described above, or fragments thereof. Such fragments can, for example, be at least about 5, 10, 15, 20, 25, 50, 75, 100, 150, 200, 250, 300, 350, 400, 450, 500, 550, 600, 650, 700, 750, 800, 850, or 900 contiguous or non-contiguous amino acids of the LGR4 polypeptide, or any number of contiguous or non-contiguous amino acids in between any of the aforementioned lengths.

In some embodiments the antibodies comprise a sequence that is 80%, 81%, 82%, 83%, 84%, 85%, 86%, 87%, 88%, 89%, 90%, 91%, 92%, 93%, 94%, 95%, 96% 97%, 98%, 99%, or 100% identical to the sequence of the antibody sequences described herein. In some embodiments the antibodies comprise a sequence that is 100% identical to the antibody sequences described herein over a span of 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, or 118 residues of the heavy chain, light chain, or variable domains of the above sequences.

In some embodiments the antibodies comprise a sequence that is 80%, 81%, 82%, 83%, 84%, 85%, 86%, 87%, 88%, 89%, 90%, 91%, 92%, 93%, 94%, 95%, 96% 97%, 98%, 99%, or 100% identical to the antibody sequences. In some embodiments the antibodies comprise a sequence that is 84%, 85%, 86%, 87%, 88%, 89%, 90%, 91%, 92%, 93%, 94%, 95%, 96% 97%, 98%, 99%, or 100% identical to the antibody sequences. In some embodiments the antibodies comprise a sequence that is 100% identical to the antibody sequences of over a span of 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, or 111 residues.

In some embodiments, an anti-LGR4 antibody provided herein comprises: (a) a heavy chain CDR1 comprising variants of the above sequences having 1, 2, 3, or 4 amino acid substitutions. The antibody may also have a heavy chain CDR2 having a variant comprising 1, 2, 3, or 4 amino acid substitutions. The antibody may also have a heavy chain CDR3 having a variant comprising 1, 2, 3, or 4 amino acid substitutions. In addition to these modifications of the heavy chain, the antibody may also have a light chain CDR1 having a variant comprising 1, 2, 3, or 4 amino acid substitutions. The antibody may also have a light chain CDR2 having a variant comprising 1, 2, 3, or 4 amino acid substitutions. The antibody may also have a light chain CDR3 having 1, 2, 3, or 4 amino acid substitutions. In some embodiments, the amino acid substitutions are conservative amino acid substitutions.

In some embodiments, an anti-LGR4 antibody provided herein comprises an antibody which comprises a heavy chain variable region having at least 80% or 90% sequence identity to the sequences described herein. The antibody may also have a light chain variable region having at least 80% or 90% sequence identity to the antibody sequences described herein.

The percent identity of two amino acid sequences (or two nucleic acid sequences) can be determined, for example, by aligning the sequences for optimal comparison purposes (e.g., gaps can be introduced in the sequence of a first sequence). The amino acids or nucleotides at corresponding positions are then compared, and the percent identity between the two sequences is a function of the number of identical positions shared by the sequences (i.e., % identity=# of identical positions/total # of positions×100). The actual comparison of the two sequences can be accomplished by well-known methods, for example, using a mathematical algorithm. A specific, non-limiting example of such a mathematical algorithm is described in Karlin et al., Proc. Natl. Acad. Sci. USA, 90:5873-5877 (1993), which is incorporated herein by reference in its entirety. Such an algorithm is incorporated into the BLASTN and BLASTX programs (version 2.2) as described in Schaffer et al., Nucleic Acids Res., 29:2994-3005 (2001), which is incorporated herein by reference in its entirety. When utilizing BLAST and Gapped BLAST programs, the default parameters of the respective programs (e.g., BLASTN) can be used. See http://www.ncbi.nlm.nih.gov, as available on Apr. 10, 2002. In one embodiment, the database searched is a non-redundant (NR) database, and parameters for sequence comparison can be set at: no filters; Expect value of 10; Word Size of 3; the Matrix is BLOSUM62; and Gap Costs have an Existence of 11 and an Extension of 1.

Several embodiments also encompass variants of the above described antibodies, including any one of the anti-LGR4 antibodies designated as 8F3 and 1C5 produced and described in the Examples below, comprising one or more amino acid residue substitutions in the variable light ($V_L$) domain and/or variable heavy ($V_H$) domain. Several also encompass variants of the above described antibodies with one or more additional amino acid residue substitutions in one or more $V_L$ CDRs and/or one or more $V_H$ CDRs. The antibody generated by introducing substitutions in the $V_H$ domain, $V_H$ CDRs, $V_L$ domain and/or $V_L$ CDRs of the above described antibodies can be tested in vitro and in vivo, for example, for its ability to bind to LGR4 (by, e.g., immunoassays including, but not limited to ELISAs and BIAcore).

Various embodiments include antibodies that specifically bind to LGR4 comprising derivatives of the $V_H$ domains, $V_H$ CDRs, $V_L$ domains, or $V_L$ CDRs of anti-LGR4 antibodies, such as any one of the anti-LGR4 antibodies produced and described in the Examples below, that specifically bind to LGR4. Standard techniques known to those of skill in the art can be used to introduce mutations (e.g., additions, deletions, and/or substitutions) in the nucleotide sequence encoding an antibody, including, for example, site-directed mutagenesis and PCR-mediated mutagenesis are routinely used to generate amino acid substitutions. In one embodiment, the $V_H$ and/or $V_L$ CDRs derivatives include less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the original $V_H$ and/or $V_L$ CDRs. In another embodiment, the $V_H$ and/or $V_L$ CDRs derivatives have conservative amino acid substitutions (e.g. supra) made at one or more predicted non-essential amino acid residues (i.e., amino acid residues which are not critical for the antibody to specifically bind to LGR4). Alternatively, mutations can be introduced randomly along all or part of the $V_H$ and/or $V_L$ CDR coding sequence, such as by saturation mutagenesis, and the resultant mutants can be screened for biological activity to identify mutants that retain activity. Following mutagenesis, the encoded antibody can be expressed and the activity of the antibody can be determined.

Several embodiments also encompass antibodies that specifically bind to LGR4 or a fragment thereof, said antibodies comprising an amino acid sequence of a variable heavy chain and/or variable light chain that is at least 45%, at least 50%, at least 55%, at least 60%, at least 65%, at least 70%, at least 75%, at least 80%, at least 85%, at least 90%, at least 95%, or at least 99% identical to the amino acid sequence of the variable heavy chain and/or light chain of any of the antibodies described herein including any one of the anti-LGR4 antibodies produced and described in the Examples below.

Another embodiment includes the introduction of conservative amino acid substitutions in any portion of an anti-LGR4 antibody. It is well known in the art that "conservative amino acid substitution" refers to amino acid substitutions that substitute functionally-equivalent amino acids. Conservative amino acid changes result in silent changes in the amino acid sequence of the resulting peptide. For example, one or more amino acids of a similar polarity act as functional equivalents and result in a silent alteration within the amino acid sequence of the peptide. Substitutions that are charge neutral and which replace a residue with a smaller residue may also be considered "conservative substitutions" even if the residues are in different groups (e.g., replacement of phenylalanine with the smaller isoleucine). Families of amino acid residues having similar side chains have been defined in the art. Several families of conservative amino acid substitutions are shown in Table 1.

TABLE 1

| Family | Amino Acids |
|---|---|
| non-polar | Trp, Phe, Met, Leu, Ile, Val, Ala, Pro |
| uncharged polar | Gly, Ser, Thr, Asn, Gln, Tyr, Cys |
| acidic/negatively charged | Asp, Glu |
| basic/positively charged | Arg, Lys, His |
| Beta-branched | Thr, Val, Ile |
| residues that influence chain orientation | Gly, Pro |
| aromatic | Trp, Tyr, Phe, His |

Blocking Cancer Stem Cell Growth with Anti-LGR4 Antibodies

Several embodiments are drawn to blocking cancer stem cell growth in vitro and in vivo with anti-LGR4 antibodies. In some embodiments, a method of blocking cancer stem cell growth comprises administering an effective amount of an anti-LGR4 antibody to cancer stem cells, wherein the effective amount of the anti-LGR4 antibody is sufficient to reduce growth of the cancer stem cells.

In some embodiments, a method of blocking cancer stem cell growth comprises administering an effective amount of an anti-LGR4 antibody to cancer stem cells, wherein the effective amount of the anti-LGR4 antibody is sufficient to reduce or block proliferation, or reduce or block the growth, of the cancer stem cells.

In some aspects, an effective amount of an anti-LGR4 antibody is administered to cancer stem cells in vitro. In other aspects, an effective amount of an anti-LGR4 antibody is administered to cancer stem cells in a patient in need of treatment thereof, in vivo.

In several embodiments, antibodies against LGR4 are used in methods of inhibiting LGR4 signaling without inhibiting R-Spo binding to LGR4. In several embodiments, antibodies against LGR4 are used in methods of inhibiting LGR4 signaling without inhibiting R-Spo signaling through LGR4. In several embodiments, antibodies against LGR4 are used in methods of inhibiting LGR4 signaling without inhibiting R-Spo binding to LGR4 or signaling through LGR4. In several embodiments, antibodies against LGR4 are used in methods of inhibiting LGR4 signaling through Wnt. In several embodiments, antibodies against LGR4 are used in methods of inhibiting LGR4 signaling through Wnt that is independent of RSpo signaling.

As used herein, the term "cancer stem cell(s)" refers to a cell that can proliferate extensively or indefinitely and give rise to a large proportion of cancer cells in a cancer. In some aspects, the large proportion of cancer cells represents a majority of the cancer cells in a given cancer. For illustration, but not limitation, a cancer stem cell(s) can be a founder of a tumor or a progenitor of the cancer cells that comprise the majority of a cancer's mass. In some aspects, cancer stem cells refer to cells that divide to form one or more tumors when implanted into an immunocompromised individual, in the absence of any additional mutation to the cells or introduction of exogenous cell proliferation-inducing or carcinogenic agents. In some aspects cancer stem cells divide to yield additional cancer stem cells as well as terminally differentiated cancer cells or cancer tissue.

In some embodiments cancer stem cell growth, proliferation, or viability is blocked without interfering with LGR4-RSpo binding or signaling. In some embodiments cancer stem cell growth, proliferation, or viability is blocked without interfering with LGR4-RSpo binding or signaling through blocking or inhibiting LGR4 signaling through Wnt.

As used with respect to blocking cancer stem cell growth, the term "effective amount" refers to an amount of anti-LGR4 antibody sufficient to reduce the growth of cancer stem cells by any degree. Any assay known in the art can be used to measure cancer stem cell growth. For example, cancer stem cell growth can be measured by colony count, total cell count, or volume/size of a cell population or colony. In several embodiments, cancer stem cell growth can be measured by the tumor sphere growth assay described below in Example 1.

In certain embodiments, an effective amount of an anti-LGR4 antibody can block cancer stem cell growth as measured by at least a 5%, 10%, 15%, 20%, 30%, 40%, 50%, 60%, 70%, 80%, 90%, 95%, 96%, 97%, 98%, 99%, or 100% reduction in the cancer stem cell population or tumorsphere growth, or any percentage in between any of the aforementioned numbers.

For example, in some embodiments, an effective amount of an anti-LGR4 antibody can block cancer stem cell growth as measured by at least about 5%-99%, a 5%-80%, a 5 to 40%, a 10% to 99%, a 10 to 80%, a 10-60%, a 10%-40%, a 20 to 99%, a 20%-80%, a 20%-60%, a 20%-40%, a 50%-98%, 50%-80%, or a 60%-99% reduction in the cancer stem cell population or tumorsphere growth.

In other embodiments, the effective amount of an anti-LGR4 antibody can block cancer stem cell growth as measured by at least about a 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 4.0, 4.5, 5.0, 10, 25, 50, 75, 100, 200, or 1000-fold reduction in the cancer stem cell population or tumorsphere growth, or any fold-reduction in between any of the aforementioned numbers.

In some embodiments, the effective amount of an anti-LGR4 antibody sufficient to block cancer stem cell growth by any degree described above is in a concentration of about 1 nM, 50 nM, 75 nM, 100 nM, 150 nM, 200 nM, 250 nM, 300 nM, 350 nM, 400 nM, 500 nM, 550 nM, 600 nM, 700 nM, 800 nM, 900 nM, 1 µM, 50 µM, 75 µM, 100 µM, 150 µM, 200 µM, 250 µM, 300 µM, 350 µM, 400 µM, 500 µM, 550 µM, 600 µM, 700 µM, 800 µM, 900 µM, 1 mM, 5 mM, 10 mM, 15 mM, 20 mM, 25 mM, 30 mM, 35 mM, 40 mM, 45 mM, 50 mM, 75 mM, 100 mM, 200 mM, 300 mM, 400 mM, 500 mM, 600 mM, 700 mM, 800 mM, 900 mM, 1000 mM, 1 M, 5 M, 10 M, 15 M, 20 M, 25 M, 30 M, 35 M, 40 M, 45 M, 50 M, 75 M, 100 M, or any number in between any two of the aforementioned concentrations.

In some embodiments, an anti-LGR4 antibody provided herein binds human LGR4 with a KD of less than about 200 nM, less than about 100 nM, less than about 80 nM, less than about 50 nM, less than about 20 nM, less than about 10 nM, less than about 1 nM, and a range between any of the foregoing values. In some embodiments, an anti-LGR4 antibody provided herein binds LGR4 with an affinity less than about 10 nM, 5 nM, 4 nM, 3 nM, 2 nM, 1 nM, and within a range of any of the foregoing values. In some embodiments, an anti-LGR4 antibody provided herein binds LGR4 with an affinity greater than about 0.0001 nM, 0.001 nM, 0.01 nM, and within a range of any of the foregoing values.

In some embodiments, an anti-LGR4 antibody provided herein does not significantly disrupt the binding of R-spondin (RSPO) proteins to LGR4. In some embodiments, an anti-LGR4 antibody provided herein does not bind a RSPO-LGR4 binding site. In some embodiments, an anti-LGR4 antibody provided herein does not compete with RSPO for binding to LGR4. In some embodiments, an anti-LGR4 antibody provided herein does not significantly disrupt RSPO activation of Wnt signaling. In some embodiments, an anti-LGR4 antibody provided herein can disrupt Some embodiments include methods of inhibiting Wnt/β-catenin signaling in a cell. Some of the foregoing methods can include contacting the cell with an effective amount of an anti-LGR4 antibody as described herein. In some embodiments, the cell is a tumor cell. In some embodiments, the cell can include a breast tumor cell, a lung tumor cell, a colorectal tumor cell, or a pancreatic tumor cell. In some embodiments, the tumor cell can express elevated levels of LGR4 protein. In some embodiments, the anti-LGR4 antibody described herein inhibits growth of the tumor, for example, by reducing the number and/or frequency of cancer stem cells.

Some embodiments include methods of treating cancer comprising administering a therapeutically effective amount of an anti-LGR4 antibody to a subject in need thereof. In some embodiments, the cancer is selected from lung cancer, ovarian cancer, pancreatic cancer and colorectal cancer, breast cancer, such as triple negative breast cancer. In some embodiments, the colorectal cancer comprises an inactivating mutation in the adenomatous polyposis coli (APC) gene, does not comprise an inactivating mutation in the APC gene, or comprises a wild-type APC gene. In some embodiments, the cancer comprises elevated levels of LGR4 protein. In some embodiments, the cancer is colon cancer that expresses elevated levels of LGR4. In some embodiments, the cancer is a pancreatic cancer that expresses elevated levels of LGR4, In some embodiments, the cancer is a breast cancer that expresses elevated levels of LGR4.

Some embodiments include methods of treating a disease in a subject wherein the disease is associated with activation of β-catenin, and/or aberrant β-catenin signaling. Some embodiments include administering a therapeutically effective amount of an anti-LGR4 antibody to a subject in need thereof.

Some embodiments include methods of treating a disease by administering a therapeutically effective amount of an anti-LGR4 antibody to a subject in need thereof in combination with at least one additional therapeutic agent. In some embodiments, the additional therapeutic agent comprises a chemotherapeutic agent. In some embodiments, the additional therapeutic agent comprises a biologic agent. Some embodiments include administering an anti-LGR4 antibody in combination with a chemotherapeutic agent and a biologic agent. In some embodiments, administering an anti-LGR4 antibody in combination with a chemotherapeutic agent can decrease the expression level of LGR4 in a cancer, such as a tumor. Some embodiments of the methods provided herein include determining the level of LGR4 protein expression in a tumor or cancer.

Other embodiments include a method of identifying a subject for treatment with an anti-LGR4 antibody. Some embodiments include determining if the subject has a tumor with an elevated expression level of LGR4 as compared to the expression level of the same LGR4 protein in normal tissue. Some embodiments include selecting a subject for treatment if the tumor has an elevated level of LGR4 expression above a predetermined threshold value. Some embodiments also include determining if the subject has a tumor that comprises an inactivating mutation in the APC gene. Some embodiments also include selecting a subject for treatment if the tumor has an inactivating mutation in the APC gene.

Having generally described embodiments drawn to antibodies against LGR4, hybridomas or other cell lines expressing such antibodies, nucleic acids and vectors comprising nucleic acids encoding for such antibodies, and methods of blocking cancer stem cell growth with such antibodies, a further understanding can be obtained by reference to certain specific examples which are provided for purposes of illustration only and are not intended to be limiting.

EXAMPLES

Example 1

LGR4 is Over-Expressed in Tumors

Figure 1:
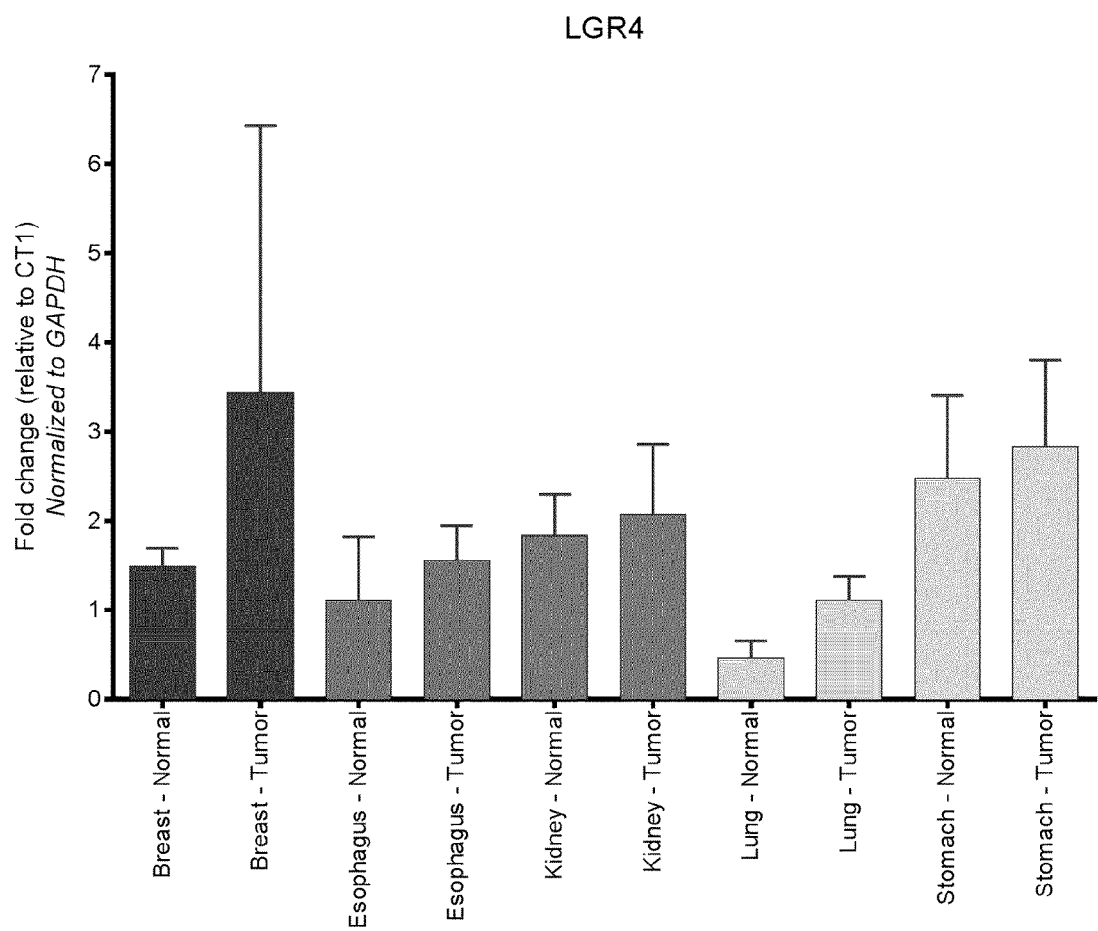
FIG. 1 is a bar graph depicting LGR4 expression in tumors and normal tissues. Shown is a sample of microarray data from normal and malignant tissue human samples.

LGR4 expression levels in human normal and tumor tissues were evaluated using Origene cDNA panels (cat# CSRT303) and qPCR. Expression levels were determined relative to levels in human CT1 tumor cells, and normalized against GAPDH. LGR4 expression was found to be significantly increased in breast and lung tumors over normal tissues. FIG. 1 is a bar graph depicting a comparison of LGR4 expression levels in breast, esophagus, kidney, lung and stomach tissues, from tumor and normal tissue samples.

Example 2

Knockdown of LGR4 Appears to Significantly Reduce Breast Cancer Sphere Formation An in vitro method was developed to maintain and propagate cancer stem cells based on the observation that normal and malignant stem cells from neural and breast tissue can be maintained in non-adherent neurosphere or mammosphere cultures. These sphere cultures are grown under "cancer stem cell" conditions: ultra-low-attachment plates to ensure non-adherent cultures, with no serum and supplemented with growth factors (i.e. EGF, bFGF) and anti-differentiation factors such as Leukemia-inhibitor-factor (LIF). Neuro- and mammospheres have stem cell features such as the capacity for self-renewal and differentiation. Sphere cultures established from malignant tumor tissue, termed "tumorspheres", are highly tumorigenic in vivo, in addition to having self-renewal and differentiation capacity. Tumorspheres also have increased resistance to chemotherapeutic reagents, indicating that they are a relevant model for cancer drug development.

Figure 2:
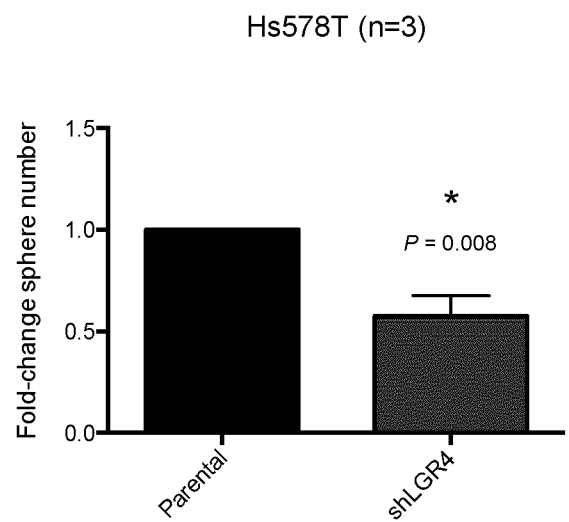
FIG. 2 is a bar graph depicting shRNA-mediated knock-down of LGR4 in breast cancer cell line Hs578T tumorspheres.

Short hairpin RNA (shRNA) mediated knockdown of LGR4 in breast cancer cell line Hs578T tumorspheres was examined. Hs578T cells were infected with lentiviral particles carrying shRNA targeting LGR4 or an empty vector control (Sigma). Infected cells were selected with appropriate antibiotic treatment 72 hours after infection. Knockdown of LGR4 expression was confirmed by quantitative PCR (qPCR) following expansion of antibiotic-selected cells. The ability of shRNA-expressing cells to form spheres in serum-free CSC culture was examined. Reducing the expression of LGR4 through shRNA significantly decreased the ability of Hs578T cells to form spheres (n=3). FIG. 2 shows that shRNA against LGR4 substantially reduced sphere formation of Hs578T cells.

Example 3

Figure 3:
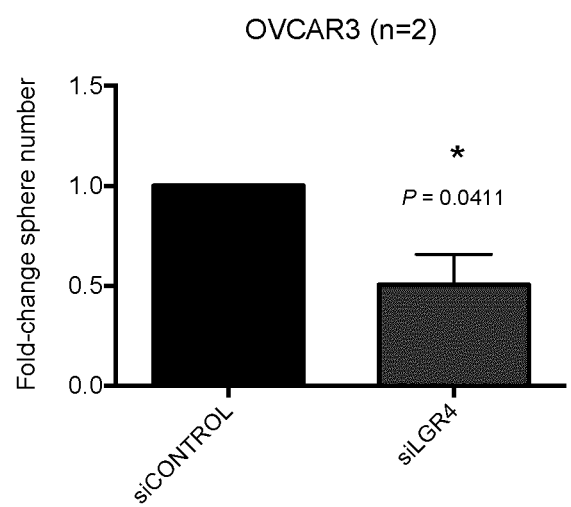
FIG. 3 is a bar graph depicting shRNA-mediated knock-down of LGR4 in ovarian cancer cell line OVCAR3 tumorspheres.

Knockdown of LGR4 Appears to Significantly Reduce Sphere Formation in OVCAR3 Ovarian Adenocarcinoma Cells The effect of suppressing the expression of LGR4 on ovarian adenocarcinoma cell line OVCAR3 tumorspheres was also examined. OVCAR3 cells were transiently transfected with siRNA targeting LGR4 or a negative control siRNA (Invitrogen). Knockdown of LGR4 expression was confirmed by qPCR. The ability of siRNA-transfected cells to form spheres in serum-free CSC culture was examined. A reduction in LGR4 expression from the siRNA against LGR4 significantly decreased the ability of OVCAR3 cells to form spheres (n=2). See FIG. 3.

Example 4

LGR4 Expression is Significantly Increased in Tumors after Treatment with Chemotherapeutic Drugs To investigate if chemotherapeutic drug treatment altered LGR4 expression in tumors, a number of patient-derived tumors were treated with relevant standard of care treatments. In a colorectal patient derived tumor model, RNA was isolated from tumors treated with either PBS or chemotherapy (FOLFIRI). cDNA was synthesized from 1000 ng RNA per sample and qPCR was run in duplicate for LGR4 and GAPDH expression. Statistical significance was determined using unpaired t test (Graphpad Prism 6). LGR4 gene expression was found to be significantly higher for the FOLFIRI treatment vs PBS (p<0.0001).

In a triple negative breast cancer patient-derived tumor model, the cancer stem cell populations in tumors from mice treated with 50 mg/kg carboplatin and 100 mg/kg Abraxane or 50 mg/kg carboplatin and 50 mg/kg Abraxane were examined by flow cytometry. The percentage of LGR4 positive cells was found to be increased in the 50 mg/kg carboplatin and 100 mg/kg Abraxane treatment group but not the 50 mg/kg carboplatin and 50 mg/kg Abraxane treatment group.

Example 5

Production of Rat Antibodies to Full-Length Human LGR4

To produce antibodies against the full length LGR4 receptor, rats were immunized three times with a vector encoding the full-length cDNA clone of the LGR4 gene. Blood from individual mice was screened approximately 75 days after initial immunization for antigen recognition using ELISA and FACS analysis. Approximately 10,000 clones were generated with approximately 200 positive clones selected by LGR4-CHO capture ELISA.

Hybridoma supernatants were analyzed by a cell-based ELISA (cELISA) on cells transiently transfected with the LGR4 cDNA. A goat anti-rat IgG-HRP (Southern Biotech, #3030-05) at 0.1 µg/ml was used as secondary antibody. Monoclonal antibodies (mAbs) from 5 selected subclones were purified from the hybridoma supernatant using protein A or protein G agarose chromatography for further testing. Table 2 lists several nucleotide and amino acid sequences for aspects of LGR4, and the anti-LGR4 monoclonal antibodies: 8F3 and 1C5.

TABLE 2

| SEQ ID NO. | Sequence |
| --- | --- |
| SEQ ID NO: 01 | LGR4 nucleotide sequence with signal sequence |
| SEQ ID NO: 02 | LGR4 protein sequence with signal sequence |
| SEQ ID NO: 03 | 8F3 heavy chain nucleotide sequence |
| SEQ ID NO: 04 | 8F3 light chain nucleotide sequence |
| SEQ ID NO: 05 | 8F3 heavy chain amino acid sequence |
| SEQ ID NO: 06 | 8F3 light chain amino acid sequence |
| SEQ ID NO: 07 | 1C5 heavy chain nucleotide sequence |
| SEQ ID NO: 08 | 1C5 light chain nucleotide sequence |
| SEQ ID NO: 09 | 1C5 heavy chain amino acid sequence |
| SEQ ID NO: 10 | 1C5 light chain amino acid sequence |

Example 6

LGR4 Antibodies Binds to Human LGR4

Figures 4A, 4B, 4C:
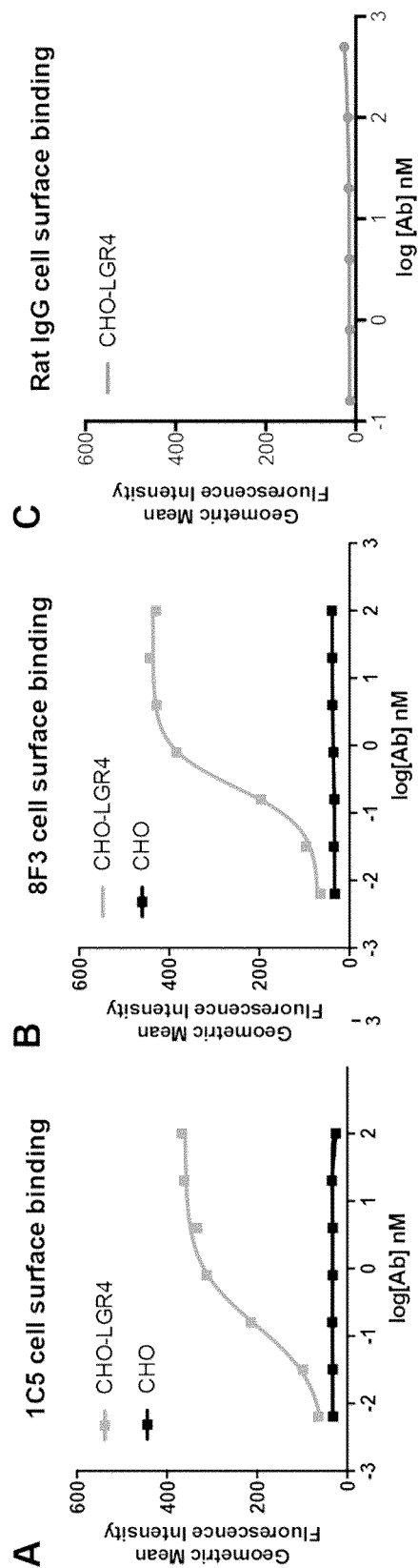
FIGS. 4A-4C are line graphs depicting binding of purified anti-LGR4 antibodies to human LGR4 overexpressed on the surface of CHO cells, with FIG. 4A showing 1C5 cell surface binding, FIG. 4B showing 8F3 cell surface binding, and FIG. 4C showing rat IgG cell surface binding.

A flow cytometry-based assay was used to measure the binding of purified anti-LGR4 antibodies 1C5 and 8F3 to recombinant human LGR4 protein overexpressed on the surface of CHO cells. CHO and CHO-LGR4 cells were stained with serial dilutions of anti-LGR4 antibodies at 4° C. Surface staining was detected with PE-conjugated anti-rat IgG secondary antibodies and analyzed on the FACSCalibur (FIG. 4A and FIG. 4B). The EC50 values of anti-LGR4 antibodies for human LGR4 binding were in the 0.15-0.50 nM range. An antibody control (pooled rat IgG) was used as a negative isotype control in these experiments as well as wild-type CHO without LGR4. The isotype control did not show any measurable binding to CHO cells expressing human (FIG. 4C) and anti-LGR4 antibodies showed no binding to CHO cells that do not express human LGR4 (FIGS. 4A and 4B).

Example 7

Figures 5A, 5B:
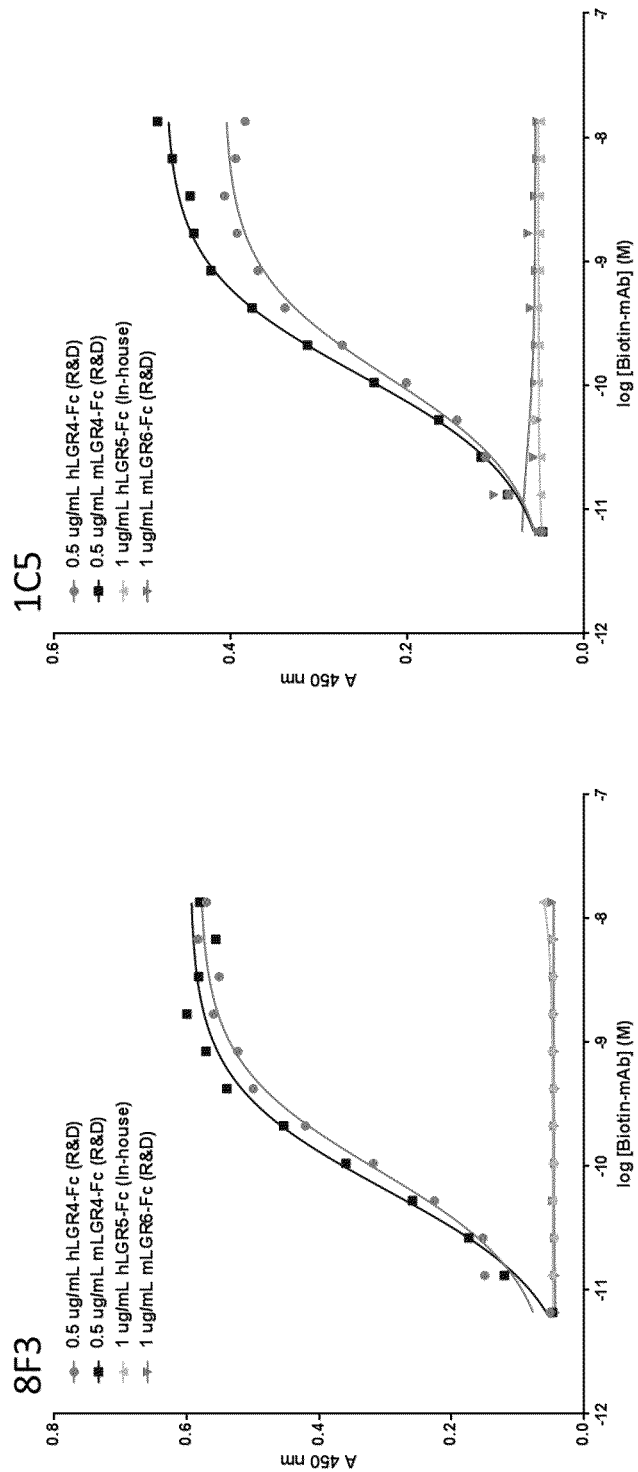
FIGS. 5A-5B are line graphs depicting binding of the anti-LGR4 antibodies to human and murine LGR4 assessed in vitro using an ELISA-based plate binding assay with FIG. 5A showing 8F3 binding and FIG. 5B showing 1C5 binding.

Binding of LGR4 Antibodies to Plate-Bound Recombinant, Human and Murine LGR4 Ectodomain Binding of the anti-LGR4 antibodies to human and murine LGR4 was assessed in vitro using an ELISA-based plate binding assay. The assay measured biotinylated antibody binding to ELISA plate-bound purified recombinant, LGR4 ectodomain-IgG-Fc fusion, with detection of LGR4-bound antibody with horseradish peroxidase-conjugated streptavidin. The EC50 values of anti-LGR4 antibodies for human LGR4 binding were in the 90-115 pM range and for murine LGR4 in the 64-120 pM range. Anti-LGR4 antibodies showed no binding to LGR5-Fc or LGR6-Fc as negative controls. Binding data from two of the antibodies, 8F3 and 1C5 are shown in FIGS. 5A and 5B, respectively.

Example 8

LGR4 Antibody Treatment have Varied Activity in In Vitro Wnt-Signaling Pathway Parental HEK-293T cells that endogenously express LGR4 were transduced with a TCF-LEF reporter vector-containing lentivirus (GFP Cignal, QIAGEN) and selected for stable expression of the reporter. Stable reporter lines were plated at 25,000 cells per well in a 96 well plate, allowed to attach overnight, serum starved and treated with antibodies or vehicle for 6 h, then treated with recombinant human Wnt3a (3 nM) and recombinant human R-spondins for 18 h. Two concentrations for each R-spondins 1, 2 or 3 and one concentration of R-spondin 4 were tested (100 pM, 300 pM, 1 nM, 3 nM or 10 nM) based on our analysis of the activity of the different R-spondins in activation of the TCF/LEF reporter cell lines. The reporter-driven GFP signal was measured on a plate reader. All experiments shown are pooled data from three independent experiments (each experiment performed in duplicate) for each R-spondin tested (data are means+SD).

Figure 6:
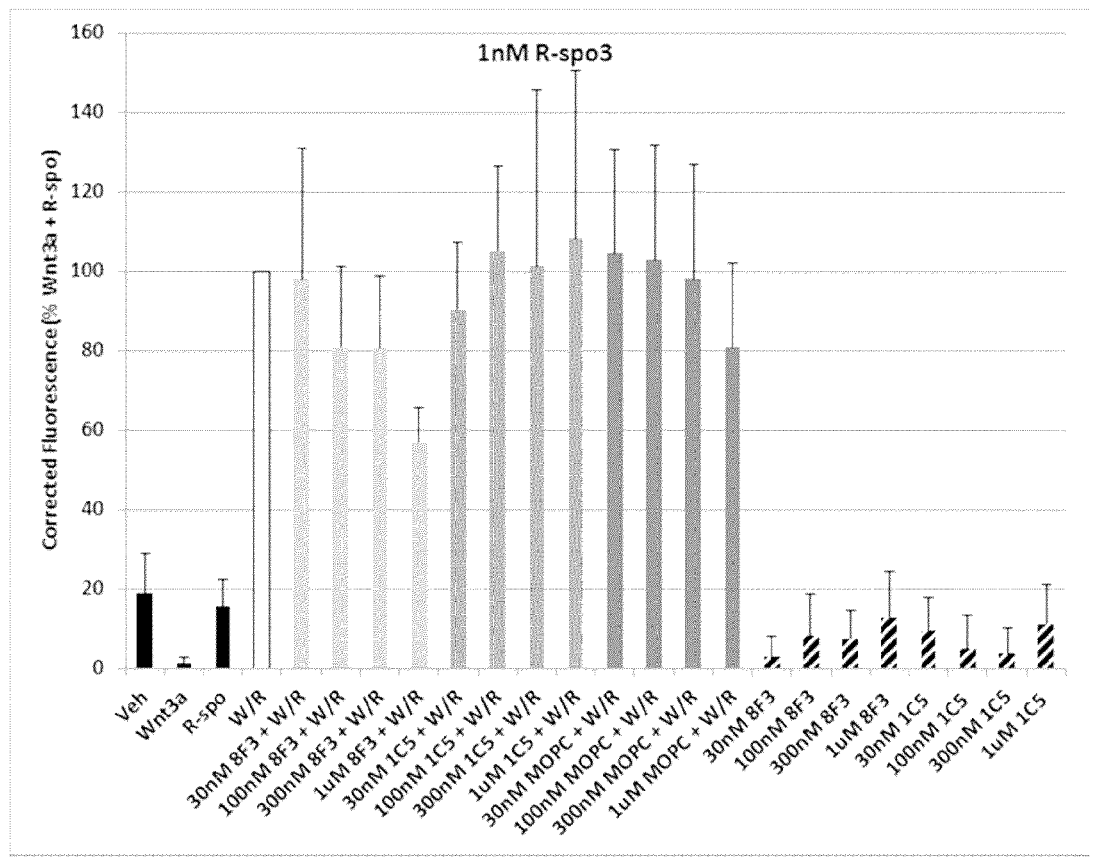
FIG. 6 is a bar graph depicting the discovery that anti-LGR4 antibodies show differential activity in a TCF-LEF reporter assay used to measure β-catenin signaling induced by RSPO and WNT3A and in the presence of increasing concentrations of anti-LGR4 antibody 8F3 and 1C5. Anti-LGR4 antibody 8F3 showed inhibition of β-catenin signaling with increasing concentration of antibody, however, antibody 1C5 did not show any inhibition.

It was discovered that increasing concentrations of soluble anti-LGR4 antibodies resulted in both inhibition (with 8F3 treatment) as well as no effect (with 1C5 treatment) on the induction of TCF/LEF promoter-driven GFP expression by the combination of Wnt3a plus Rspo1, Rspo2 or Rspo3 (FIG. 6).

Example 9

LGR4 Antibodies do not Competitively Block Binding of Soluble RSPOs to LGR4

Formation of complexes between 1C5 and 8F3 anti-human LGR4 mAbs, human LGR4, and human Rspo 4 were evaluated using a co-immunoprecipitation (co-IP) assay. Biotinylated 1C5 or 8F3 rat monoclonal antibodies were captured on streptavidin magnetic beads (Solulink, Inc., San Diego, Calif.). Immobilized antibodies were washed 2× in TBST buffer. Human LGR4-Fc (R&D Systems) was added to all co-IP reactions. Unlabeled mAb was added to the same mAb captured on the beads to show that the antibody can compete with itself for binding to LGR4. Unlabeled 1C5 mAb was also added to 8F3 mAb on the beads, and vice versa, to test for cross-competition between the 1C5 mAb and 8F3 mAb. MOPC-21 mAb (Bio X Cell, West Lebanon, N.H.) was added as a non-competitor mAb control. Finally, human Rspo 4 (R&D Systems, Inc., Minneapolis, Minn.) was added to co-IP reactions containing biotin-1C5/LGR4 or biotin-8F3/LGR4 to test whether the antibodies could compete with the Rspo4/LGR4 interaction. Co-IP reactions were incubated at room temperature for 2 hours on a shaking platform. The supernatant containing unbound proteins was discarded, and the beads were washed 3× with TBST buffer. Bound proteins were eluted with 1×SDS-PAGE loading buffer (Life Technologies, Carlsbad, Calif.), and clarified supernatant was transferred to a new vial. Each co-IP sample was resolved on a 4-20% reducing SDS-PAGE. Human LGR4-Fc was detected by western blotting using horseradish peroxidase-conjugated anti-human IgG Fc antibody.

Figure 7:
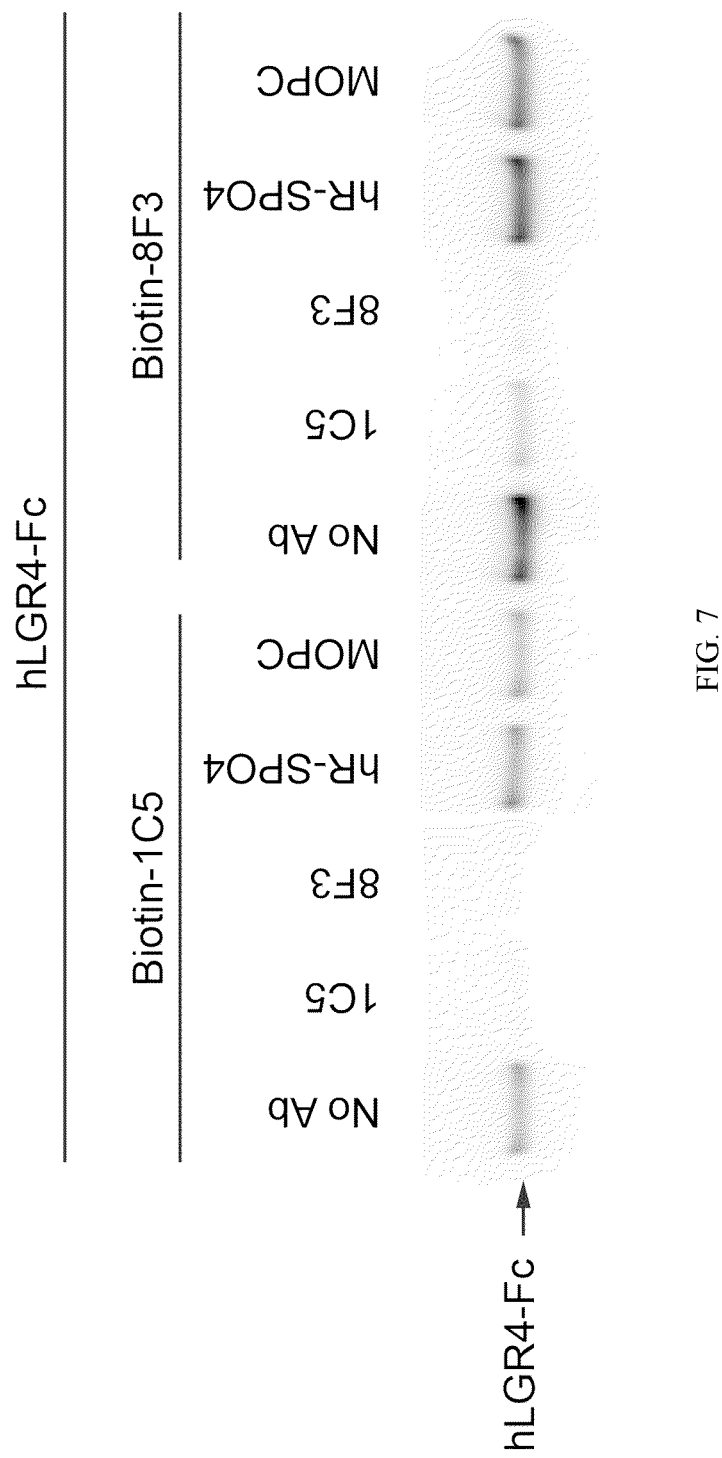
FIG. 7 is a photograph of a gel that depicts the results of a co-immunoprecipitation assay in which formation of complexes between 1C5 and 8F3 anti-human LGR4 mAbs, human LGR4, and human Rspo4 were evaluated. This gel showed that LGR4 antibodies did not competitively block binding of soluble RSPOs to LGR4.
Figure 8A:
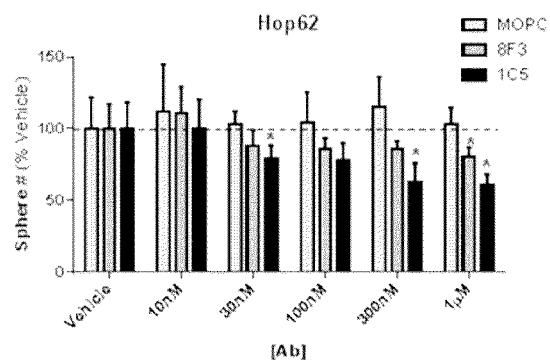
FIGS. 8A-8D are bar graphs depicting inhibition of lung (FIG. 8A), ovarian (FIG. 8C), breast (FIG. 8B) and pancreatic (FIG. 8D) cancer stem cell sphere formation in vitro by treating cells with anti-LGR4 antibodies 8F3 and 1C5.
Figure 8B:
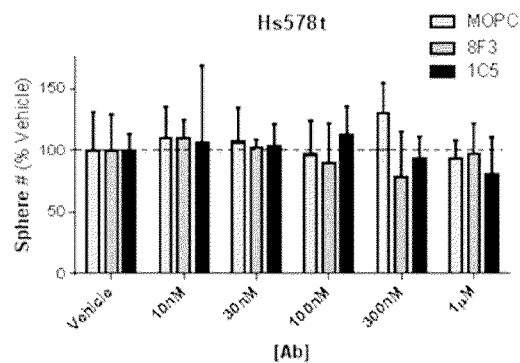
Figure 8C:
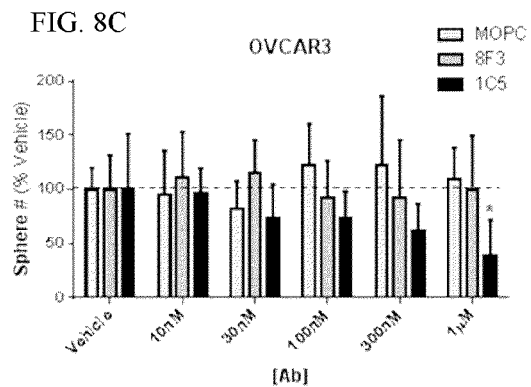
Figure 8D:
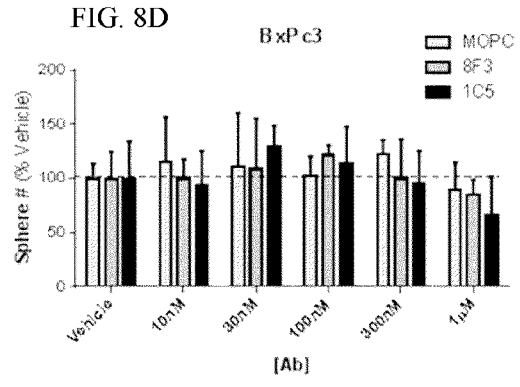

Human LGR4– was efficiently immunoprecipitated with biotinylated 1C5 and 8F3 monoclonal antibodies (FIG. 7). Unlabeled 1C5 mAb or 8F3 mAb were able to compete with themselves for binding to LGR4-Fc as demonstrated in lanes 4 and 9. Unlabeled 1C5 mAb and 8F3 mAb were also able to compete with each other suggesting that these antibodies share an overlapping epitope on LGR4. No competition was observed with non-competitor control antibody MOPC-21. Addition of Rspo 4 did not affect LGR4 precipitation with either 1C5 mAb or 8F3 mAb suggesting that R-spondins do not compete with 8F3 or 1C5/LGR4 interaction in this assay.

Example 10

LGR4 mAbs Inhibit Growth of Cancer Stem Cells In Vitro

LGR4 mAbs were tested for their ability to inhibit growth of cancer stem cells in multiple tumorsphere assays. Tumorspheres were established from multiple tumor lines (lung—HOP62; breast—Hs578T; ovarian—OVCAR3; pancreatic—BxPc3), and seeded in the presence of LGR4 mAbs, or control IgG (MOPC) at 1-2000 cells per well in ultra-low-attachment plates. These tumorspheres were considered cancer stem cells because they were grown under established cancer stem cell conditions (serum-free medium) and low-attachment plates (cells grow in suspension).

Anti-LGR4 antibody 1C5 was able to significantly inhibit both HOP62 (lung cancer) OVCAR3 (ovarian cancer) cancer stem cell/tumorsphere formation and showed some inhibition in both Hs578T (breast cancer) and BxPc3 (pancreatic cancer) tumorspheres (FIGS. 8A-8D). Anti-LGR4 antibody 8F3 showed some inhibition at the highest concentrations in inhibiting tumorsphere formation in HOP62, Hs578T and BxPc3, but was only significant in the HOP62 assay.

Example 11

Anti-LGR4 Antibody Inhibits Tumor Growth In Vivo

Triple negative breast cancer patient-derived xenograft (PDX) tumor model BBR916 was chosen to test the in vivo anti-tumor efficacy of LGR4 antibodies. Dissociated tumor cells from BBR916 tumors were injected subcutaneously into mice each in a total volume of 200 μL/mouse on day 0, and monitored twice weekly for tumor size and body weight. At day 20, subcutaneous tumors were randomized into groups of 8 mice when tumors reached 120 mm$^3$. Antibodies were given IP at 15 mg/kg, 2 times per week. PBS and MOPC-21 (Bio X Cell, West Lebanon, N.H.) antibody (15 mg/kg) were used as controls.

Figure 9:
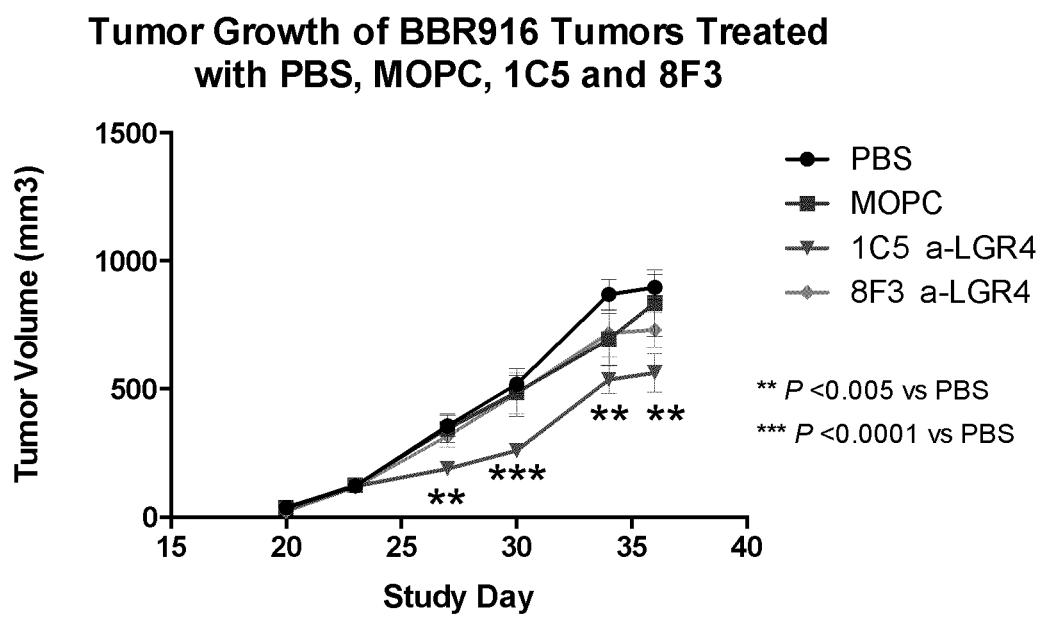
FIG. 9 is a line graph that depicts inhibition of tumor growth with anti-LGR4 antibody 1C5. Triple negative breast cancer patient-derived xenograft (PDX) tumor model BBR916 were treated with anti-LGR4 antibodies 1C5 (-▼-), 8F3 (-◇-), a control antibody MOPC (-■-), or vehicle control PBS (-●-). Data is shown as tumor volume (mm3) over study days.

Anti-LGR4 antibody 1C5 showed significant anti-tumor activity after two doses (47% tumor growth inhibition (TGI)) and after 4 doses (33% TGI) compared to MOPC antibody control. Anti-LGR4 antibody 8F3, which had shown reduction of RSPO-driven Wnt signaling showed no significant activity (FIG. 9).

Example 12

LGR4 Antibody Treatment Reduces Cancer Stem Cell Populations

Figure 10A:
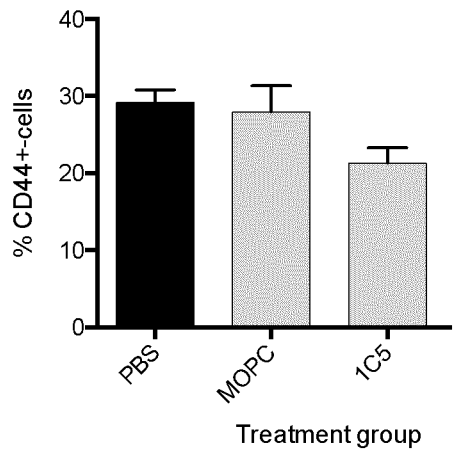
FIGS. 10A, and 10B are bar graphs showing reduction of cancer stem cell populations in treated tumors from a triple negative breast cancer PDX as defined by CD44+ (FIG.
Figure 10B:
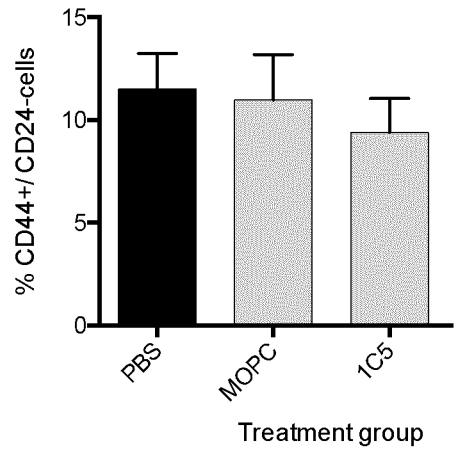

Flow cytometric analysis was used to determine the reduction of cancer stem cell populations in treated tumors from the triple negative breast cancer PDX. Cells from 8 individual tumors were stained with a variety of antibodies against stem cell specific markers CD44+ and CD44+/CD24−. Tumors were dissociated and viable cells were counted. Dissociated cells were used for analysis of human-specific cell surface stem cell marker expression by flow cytometry (FIGS. 10A and 10B).

It was discovered that there was a decrease in the cancer stem cell populations as defined by CD44+ and CD44+/CD24− subpopulations in the 1C5 treated tumors compared to PBS or MOPC treated cells.

Example 13

LGR4 mAb Treatment Reduces Cancer Stem Cell Frequency In Vivo in Primary Colon Tumors Having K-Ras, PI3K, PTEN, and p53 Mutations The CT1 primary CRC xenograft model was derived from a patient with stage IV metastatic colon cancer and has low expression of LGR4. DNA sequencing of this tumor identified common colon cancer mutations in multiple genes including K-Ras, PI3K, PTEN, p53 and APC. Low passage CT1 tumorspheres maintained in culture under serum-free conditions were injected into mice in Matrigel subcutaneously on day 0, and monitored twice weekly for tumor size and body weight. CT1 subcutaneous tumors were randomized into groups of 10 mice when tumors reached 120 mm$^3$. Mice were treated with PBS, antibody control MOPC or anti-LGR4 antibodies 8F3 or 1C5. Mice were dosed BIW at 15 mg/kg for 2.5 weeks (5 doses total). Anti-LGR4 antibodies showed limited anti-tumor activity compared to PBS and MOPC antibody controls during the course of 4 doses (15 mg/kg, twice weekly).

To determine the reduction of cancer stem cell frequency in these treated tumors, isolated CT1 tumor cells from control and LGR4 antibody treatments were harvested, pooled, dissociated and re-implanted in a limiting dilution secondary transplant assay to measure cancer stem cell frequency. The assay is a functional in vivo measurement of self-renewal capacity, a key component of any stem cell. For each treatment group, 10 mice were implanted with 10, 30 or 100 cells. Tumor formation (i.e. tumor take) and growth rates were monitored on a bi-weekly basis for 4 weeks. To calculate the frequency of cancer stem cells in each treatment group, linear regression analysis was performed with Prism GraphPad™ to calculate the frequency of cancer stem cells in each treatment group.

Tumor re-growth from 1C5 but not 8F3 LGR4 antibody treated tumors was inhibited. Only 1 out of 10 mice implanted with 1C5 treated tumors in the 30-cell group developed tumors and no tumors were formed in the 10-cell group after 33 days post-implant. In contrast, 5/10 of mice implanted with control treated tumors (30 cell group) and 3/10 of mice in the 10 cell group formed tumors (FIG. 11). Linear regression analysis showed a 1.5-fold reduction in the number of CSCs after LGR4 antibody treatment compared to controls.

Example 14

Administration of Anti-LGR4 Antibodies to a Human Patient Suffering from Breast Cancer A population of human patients suffering from breast cancer is treated with chemotherapy and tumor volume is monitored. It is observed that average tumor volume ceases to expand and in fact decreases upon initiation of chemotherapy. Following an extended duration of time, the tumor volume stabilizes and eventually begins to increase. A second human patient population suffering from breast cancer is treated with chemotherapy co-administered with anti-LGR4 antibodies. Again, average tumor volume is monitored. It is observed that tumor volume ceases to expand and in fact decreases upon initiation of chemotherapy. It is observed that tumor volume decreases to a minimum volume that is substantially lower than that of the first population. It is also found that tumor size remains low for a substantially extended period of time relative to the first population.

Example 15

Administration of Anti-LGR4 Antibodies to a Human Patient Suffering from Breast Cancer A first population of human patients suffering from breast cancer is administered chemotherapy alone. A second population of human patients suffering from breast cancer is administered chemotherapy in combination with anti-LGR4 antibodies. The first population demonstrates a temporary reduction in tumor size and growth, after which tumor growth resumes and symptoms return. Tumor growth after chemotherapy treatment is recalcitrant to subsequent chemotherapy treatments. The second population demonstrates reduction in tumor size to a basal level and cessation of tumor growth. Tumor growth does not resume during or upon completion of a treatment regimen. After completion of the regimen, growth does not return and symptoms of the cancer are no longer present in the second population.

Example 16

Administration of Anti-LGR4 Antibodies to a Human Patient Suffering from Breast Cancer Increases Survival A first population of human patients suffering from breast cancer is administered chemotherapy alone. A second population of human patients suffering from breast cancer is administered chemotherapy in combination with anti-LGR4 antibodies. Patient survival at a set duration after treatment (1 year) is monitored. It is observed that patient survival in the second population is substantially higher than patient survival in the first population. That is, a significantly higher proportion of the second population survives past the first year after treatment as compared to the survival rate of the first population. Similar observations are made at later intervals, and it is observed that among survivors at the first interval, members of the second group are significantly more likely to survive to a second interval (2 years after treatment) that are members of the first group alive at 1 year post treatment.

Example 17

Administration of Anti-LGR4 Antibodies to a Human Patient Suffering from Colon Cancer Decreases Side Effects A first population of human patients suffering from colon cancer is administered chemotherapy and an anti-LGR4 antibody that blocks LGR4-RSPO binding and signaling. A second population of human patients suffering from colon cancer is administered chemotherapy and anti-LGR4 antibodies. The first population demonstrates non-therapeutic side effects associated with the interference of RSPO1 signaling through LGR4. These side-effects are detrimental to patient health. The second population, administered anti-LGR4 antibodies in combination with chemotherapy, does not demonstrate non-therapeutic side effects associated with the interference of RSPO1 signaling through LGR4.

Example 18

Humanization of LGR4 Antibody

Human germline sequences were used as the acceptor frameworks for humanizing the rat antibody 1C5. To find the closest germline sequences, the most similar expressed light chain and the most similar heavy chain were identified in a database of germline sequences by NCI IgBLAST (ncbi.nlm.nih.gov/igblast/). In this search the CDR sequences of 1C5 were masked. The selection of the most suitable expressed sequence included checking for sequence identity of the canonical and interface residues. In addition, fixed VL/VH framework pairs, as determined by favorable expression and biophysical characteristics, were selected as acceptors for the rat 1C5 CDRs.

In order to identify potential structural conflicts in key structural framework residues between the humanized sequence and the parent rat monoclonal antibody 1C5 sequence, a three-dimensional model was generated. A composite of antibody structures was used to create a identity model with grafted candidate humanized sequences followed by molecular energy minimization. Structural analysis using computer software was used to identify residues that could potentially negatively impact proper folding. From this analysis, five candidate VH chains were constructed that included the parental 1C5 rat antibody CDRs. Each candidate VH chain was fused in-frame to the human IgG1 constant region and was chemically synthesized. Similarly, three candidate VL chains were constructed that included the parental 1C5 rat antibody CDRs. Each candidate VL chain was fused in-frame to the human kappa constant region and was chemically synthesized.

Selected candidate variant humanized heavy and light chain combinations were tested for functionality by co-transfection into mammalian cells. Each of the five candidate humanized 1C5 heavy chains described above were co-transfected with each of the candidate 1C5 light chains into HEK 293 cells. Recombinant IgG in the conditioned media was purified and assayed for LGR4 antigen binding activity by traditional and competitive ELISA. The 1C5 candidate heavy chain/light chain combinations (humanization variant) known as 1C5HE and 1C5HG, which exhibited the most robust binding, were selected for affinity maturation. Table 3 lists 1C5HE and 1C5HG sequences for VL and VH domains. Table 4 lists parental 1C5 VL CDRs, and parental 1C5 VH CDRs.

TABLE 3

| SEQ ID NO: | Domain | Sequences |
|---|---|---|
| SEQ ID NO: 11 | 1C5HE and 1C5HG VL domain | EIVMTQSPATLSVSPGERATLSCKASQNINK NLDWYQQKPGQAPRLLIYYTNNLQTGIPAR FSGSGSGTEFTLTISSLQSEDFAVYYCYQYKS GNTFGQGTKLEIK |
| SEQ ID NO: 12 | 1C5HE VH domain | QVQLVQSGAEVKKPGASVKVSCKASGYTF TSNFMHWVRQAPGQGLEWIGWIYPGDGD TEYNQKFNGKVTMTRDTSTSTVYMELSSLR SEDTAVYYCARGNSGYNWFAYWGQGTTV TVSS |

TABLE 3-continued

| SEQ ID NO: | Domain | Sequences |
|---|---|---|
| SEQ ID NO: 13 | 1C5HG VH domain | EVQLVQSGAEVKKPGESLKISCKGSGYTFTS NFMHWVRQMPGKGLEWIGWIYPGDGDTE YNQKFNGKVTISADKSISTAYLQWSSLKAS DTAMYYCARGNSGYNWFAYWGQGTTVTV SS |

CDRs are bold and underlined portions of the three listed sequences

TABLE 4

| SEQ ID NO: | Domain | Sequences |
|---|---|---|
| SEQ ID NO: 14 | 1C5 VL CDR | KASQNINKNLDW |
| SEQ ID NO: 15 | 1C5 VL CDR | LLIYYTNNLQT |
| SEQ ID NO: 16 | 1C5 VL CDR | YQYKSGNT |
| SEQ ID NO: 17 | 1C5 VH CDR | GYTFTSNFATH |
| SEQ ID NO: 18 | 1C5 VH CDR | WIGWIYPGDGDTEYNQKFNG |
| SEQ ID NO: 19 | 1C5 VH CDR | ARGNSGYNWFAY |

Example 19

Binding of Humanized LGR4 Antibodies to Plate-Bound Recombinant, Human LGR4 Ectodomain Binding of the humanized anti-LGR4 antibodies 1C5HE and 1C5HG to human and LGR4 was assessed in vitro using an ELISA-based plate binding assay. The assay measured antibody binding to ELISA plate-bound purified recombinant LGR4 ectodomain-IgG-Fc fusion (R&D Systems), with detection of LGR4-bound antibody with horseradish peroxidase-conjugated anti-human IgG-CH1 secondary antibody. The EC50 values of humanized anti-LGR4 antibodies 1C5HE and 1C5HG for human LGR4 binding were in the 500 pM-2 nM range. Binding data from the humanized 1C5HE and 1C5HG are shown in FIG. 12.

Example 20

Binding Kinetics of LGR4 Antibodies to Recombinant Human LGR4 Ectodomain

Binding kinetics of LGR4 antibodies to human and mouse LGR4 were determined using label-free plate-based Octet QK instrument (Pall ForteBio, LLC, Menlo Park, Calif.) at 30 degrees. Biotinylated 1C5 and 8F3 LGR4 antibodies were diluted to 5 µg/mL in 1×PBS and immobilized on streptavidin tips (Pall ForteBio, LLC, Menlo Park, Calif.). Plate shaking speed was 1000 rpm. The antibodies were captured on the tips for 150 sec. To establish a baseline, the tips were transferred into wells containing binding buffer (1×PBS, supplemented with 0.1% bovine serum albumin and 0.05% Tween 20) for 60 sec. Human LGR4-Fc (R&D Systems) and mouse LGR4-Fc (R&D Systems) were diluted in binding buffer to 80 nM, 40 nM, 20 nM, 10 nM, 5 nM to make a concentration series. Additionally, a buffer-only well was used as reference. 1C5 and 8F3-coated tips were transferred into wells containing human LGR4 and mouse LGR4 dilution series for 180 sec to measure receptor association. The tips were then dipped into binding buffer for 300 sec to measure receptor dissociation.

Data were collected using ForteBio Data Acquisition software v7.1 and analyzed using ForteBio Data Analysis software v7.1. Data were referenced by subtracting signal from the buffer sample, and fitted to a 1:1 binding model using global fitting with unlinked Rmax. The experiment was repeated three times. Sample curve fits, kinetic rate constants, and $K_D$ for 1C5 and 8F3 LGR4 antibodies are shown below in Table 5.

TABLE 5

| Receptor | LGR4 Antibody | $K_{on}$ (1/Ms) | $K_{off}$ (1/s) | $K_D$ (nM) |
|---|---|---|---|---|
| Human LGR4 | 1C5 | 4.38 (±0.98) E+05 | 6.35 (±1.06) E+04 | 1.47 |
| Mouse LGR4 | 1C5 | 3.39 (±0.65) E+05 | 4.40 (±1.08) E+04 | 1.31 |
| Human LGR4 | 8F3 | 3.97 (±0.50) E+05 | 1.81 (±0.55) E+04 | 0.47 |
| Human LGR4 | 8F3 | 3.57 (±0.73) E+05 | 1.55 (±0.72) E+04 | 0.47 |

Example 21

Anti-LGR4 Antibody Inhibits Triple Negative Breast Cancer Tumor Growth In Vivo

Anti-tumor efficacy of LGR4 antibodies were tested in triple negative breast cancer tumor model MDA-MB-231 LM3. MDA-MB-231-LM3 tumor cells were injected subcutaneously into mice each in a total volume of 200 µL/mouse on day 0, and monitored twice weekly for tumor size and body weight. At day 25, subcutaneous tumors were randomized into groups of 10 mice when tumors reached 180 mm³. Antibodies were given IP at 15 mg/kg, 2 times per week. PBS and MOPC-21 (BioXCell) antibody (15 mg/kg) were used as controls.

Anti-LGR4 antibody 1C5 showed significant anti-tumor activity at the end of study with 29.7% tumor growth inhibition (TGI)) compared to MOPC antibody control. Anti-LGR4 antibody 8F3, also showed significant activity at the end of the study with 25.1% TGI compared to PBS control (FIG. 13).

Example 22

Inhibition of Small Cell Lung Cancer Tumor Growth In Vivo by Anti-LGR4 Antibody

Anti-tumor efficacy of LGR4 antibody 1C5 was tested in patient derived metastatic small cell lung cancer xenograft model BMLG222. Dissociated tumor cells from BMLG222 tumors were implanted into CB.17 SCID mice in Matrigel subcutaneously, and monitored twice weekly for tumor size and body weight. When tumors reached an average of 130 mm³, mice were randomized. Mice were treated with either PBS, antibody control MOPC, or 1C5. Mice were dosed BIW at 15 mg/kg for. All mice were monitored twice weekly for body weight and tumor size, as well as overall health and appearance, until termination. 1C5 showed significant anti-tumor activity compared to PBS and MOPC antibody controls (38.7% tumor growth inhibition). See FIG. 14.

The term "comprising" as used herein is synonymous with "including," "containing," or "characterized by," and is inclusive or open-ended and does not exclude additional, unrecited elements or method steps.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. An antibody that specifically binds to a leucine-rich repeat containing G-protein-coupled receptor 4 (LGR4) polypeptide having an EC50 for LGR4binding less than 2 nM and greater than or equal to about 64 pM, and activity to inhibit growth of a neoplastic cell in vivo, wherein the antibody comprises:
   a first light chain complementarity determining region (CDR) polypeptide comprising SEQ ID NO:14;
   a second light chain CDR polypeptide comprising SEQ ID NO:15;
   a third light chain CDR polypeptide comprising SEQ ID NO: 16;
   a first heavy chain CDR polypeptide comprising SEQ ID NO:17;
   a second heavy chain CDR polypeptide comprising SEQ ID NO:18; and
   a third heavy chain CDR polypeptide comprising SEQ ID NO:19.

2. The antibody of claim 1 comprising a humanized polypeptide selected from the group consisting of a VL polypeptide comprising SEQ ID NO:11, a VH polypeptide comprising SEQ ID NO:12, and a VH polypeptide comprising SEQ ID NO:13.

3. The antibody of claim 1 comprising:
   (a) a VL polypeptide comprising SEQ ID NO:11, and
   (b) a VH polypeptide selected from the group consisting of SEQ ID NO.s:12 and 13.

4. The antibody of claim 1 comprising a polypeptide selected from the group consisting of a heavy chain comprising SEQ ID NO:09, and a light chain comprising SEQ ID NO:10.

5. The antibody of claim 1 comprising:
   (a) a heavy chain polypeptide comprising SEQ ID NO:09, and
   (b) a light chain polypeptide comprising SEQ ID NO:10.

6. The antibody of claim 1 having an EC50 for LGR4 binding of less than 1 nM.

7. The antibody of claim 1 having a $K_D$ for LGR4 binding of about 1.5 nM.

8. The antibody of claim 1 lacking activity to inhibit binding between LGR4 and a R-spondin protein.

9. The antibody of claim 1 lacking activity to inhibit binding between LGR4 and a R-spondin-4 protein.

10. The antibody of claim 1, wherein the neoplastic cell is selected from the group consisting of lung tumor cell, breast tumor cell, ovarian tumor cell, colon tumor cell, and pancreatic tumor cell.

11. The antibody of claim 1, wherein the neoplastic cell is selected from the group consisting of a triple negative breast cancer cell, a small cell lung cancer cell, a cancer stem cell, a cancer stem cell comprises CD44+ and CD44+/CD24−, and a colon cancer cell having a mutation in a gene selected from the group consisting of K-Ras, P13K, PTEN, p53 and APC.

12. The antibody of claim 1 comprising activity to inhibit growth of a tumor comprising the neoplastic cell.

13. The antibody of claim 1 comprising activity to reduce the frequency of cancer stem cells in a tumor.

14. The antibody of claim 1 comprising activity to inhibit growth of a tumor comprising the neoplastic cell by about 25% compared to the growth of a tumor not contacted with the antigen binding protein or fragment thereof.

15. The antibody of claim 1, wherein the antibody is a monoclonal antibody.

16. The antibody of claim 15, wherein the monoclonal antibody is selected from the group consisting of 1C5 and 8F3.

17. The antibody of claim 1, wherein the antibody is a humanized monoclonal antibody.

18. The antibody of claim 17, wherein the humanized monoclonal antibody is selected from the group consisting of 1C5HE and 1C5HG.

19. A monoclonal antibody that specifically binds to a leucine-rich repeat containing G-protein-coupled receptor 4 (LGR4) protein, said antibody comprising:
   a first light chain complementarity determining region (CDR) polypeptide comprising SEQ ID NO:14;
   a second light chain CDR polypeptide comprising SEQ ID NO:15;
   a third light chain CDR polypeptide comprising SEQ ID NO: 16;
   a first heavy chain CDR polypeptide comprising SEQ ID NO:17;
   a second heavy chain CDR polypeptide comprising SEQ ID NO:18; and
   a third heavy chain CDR polypeptide comprising SEQ ID NO:19.

20. The monoclonal antibody of claim 19, having an EC50 for LGR4 binding less than 2 nM.

21. A pharmaceutical composition comprising the antibody of claim 1 and a pharmaceutically acceptable carrier.

22. A method of inhibiting growth of a neoplastic cell comprising contacting the cell with the antibody of claim 1.

23. The method of claim 22, wherein the neoplastic cell is selected from the group consisting of lung tumor cell, breast tumor cell, ovarian tumor cell, colon tumor cell, and pancreatic tumor cell.

24. The method of claim 22, wherein the neoplastic cell is selected from the group consisting of a triple negative breast cancer cell, a small cell lung cancer cell, a cancer stem cell, a cancer stem cell comprising CD44+ and CD44+/CD24−, and a colon cancer cell having a mutation in a gene selected from the group consisting of K-Ras, P13K, PTEN, p53 and APC.

25. A method of treating a tumor in a subject comprising administering to the subject in need thereof an effective amount of the antibody of claim 1.

26. The method of claim 25, wherein the tumor is selected from the group consisting of lung tumor, breast tumor, ovarian tumor, colon tumor, and pancreatic tumor.

27. The method of claim 25, wherein the tumor is selected from the group consisting of a triple negative breast cancer tumor, a small cell lung cancer tumor, a population of cancer stem cells, a population of cancer stem cells comprising CD44+ and CD44+/CD24−, and a colon cancer tumor having a mutation in a gene selected from the group consisting of K-Ras, P13K, PTEN, p53 and APC.

28. The method of claim 25, wherein the antibody inhibits growth of the tumor.

29. The method of claim 25, wherein the antibody reduces the number of cancer stem cells in a tumor.

30. The method of claim 25, wherein the antibody inhibits growth of the tumor by about 25% compared to the growth of a tumor not contacted with the antigen binding protein or fragment thereof.

* * * * *